(12) United States Patent
Meimoun

(10) Patent No.: US 8,928,892 B2
(45) Date of Patent: Jan. 6, 2015

(54) WAVEFRONT ANALYSIS INSPECTION APPARATUS AND METHOD

(76) Inventor: Elie Meimoun, Jerusalem (IL)

( * ) Notice: Subject to any disclaimer, the term of this patent is extended or adjusted under 35 U.S.C. 154(b) by 401 days.

(21) Appl. No.: 13/254,845

(22) PCT Filed: Mar. 3, 2010

(86) PCT No.: PCT/IL2010/000177
§ 371 (c)(1),
(2), (4) Date: Sep. 4, 2011

(87) PCT Pub. No.: WO2010/100644
PCT Pub. Date: Sep. 10, 2010

(65) Prior Publication Data
US 2011/0311132 A1  Dec. 22, 2011

Related U.S. Application Data

(60) Provisional application No. 61/202,496, filed on Mar. 4, 2009, provisional application No. 61/292,168, filed on Jan. 5, 2010.

(51) Int. Cl.
| | | |
|---|---|---|
| *G01B 11/24* | (2006.01) | |
| *G01B 9/00* | (2006.01) | |
| *G01J 1/20* | (2006.01) | |
| *A61B 3/10* | (2006.01) | |
| *G01B 11/25* | (2006.01) | |

(52) U.S. Cl.
CPC .............. *A61B 3/1015* (2013.01); *G01B 11/25* (2013.01); *G01B 11/2509* (2013.01)
USPC .......... 356/601; 356/124; 250/201.9

(58) Field of Classification Search
None
See application file for complete search history.

(56) References Cited

U.S. PATENT DOCUMENTS

| | | | |
|---|---|---|---|
| 4,725,138 A * | 2/1988 | Wirth et al. ............... | 356/121 |
| 5,030,008 A | 7/1991 | Scott et al. | |
| 5,221,834 A * | 6/1993 | Lisson et al. ............... | 250/201.9 |
| 5,302,836 A | 4/1994 | Siu | |
| 5,855,074 A | 1/1999 | Abitbol et al. | |
| 6,176,583 B1 | 1/2001 | Sawai | |

(Continued)

FOREIGN PATENT DOCUMENTS

FR    2748322    11/1997

OTHER PUBLICATIONS

Zoltan Sarosi et al, "Detection of Surface Defects on Sheet Metal Parts by Using One-Shot deflectometry in the Infrared Range", Inframation 2010 Proceedings, pp. 210-243, 2010, ITC, Nashua.

(Continued)

*Primary Examiner* — Gordon J Stock, Jr.
(74) *Attorney, Agent, or Firm* — Daniel J. Swirsky; AlphaPatent Associates Ltd.

(57) ABSTRACT

The present invention provides high-resolution wavefront measurement systems and methods for real-time inspection of optical and geometrical properties of specular and transparent objects, the systems of the invention comprising at least one illumination apparatus, at least one imaging apparatus constructed and configured to image the object onto an image plane, at least one gradient element disposed at one of the aperture stops of the imaging apparatus; and a sensor placed in the image plane of the imaging apparatus, wherein the sensor is capable of differentiating between different areas of the gradient element thereby being adapted to provide real-time optical and geometrical data of the object.

20 Claims, 13 Drawing Sheets

(56) References Cited

U.S. PATENT DOCUMENTS

| | | | |
|---|---|---|---|
| 6,327,041 | B1 | 12/2001 | Guern |
| 6,525,302 | B2 * | 2/2003 | Dowski et al. ............ 250/201.2 |
| 6,556,706 | B1 | 4/2003 | Geng |
| 6,633,375 | B1 | 10/2003 | Veith et al. |
| 6,842,297 | B2 * | 1/2005 | Dowski, Jr. .................. 359/724 |
| 6,940,649 | B2 * | 9/2005 | Dowski, Jr. .................. 359/558 |
| 6,980,375 | B2 | 12/2005 | Nogoka |
| 7,019,826 | B2 | 3/2006 | Vook et al. |
| 7,171,037 | B2 | 1/2007 | Mahon et al. |
| 7,301,613 | B2 * | 11/2007 | Levecq et al. ................ 356/121 |
| 7,352,892 | B2 | 4/2008 | Zhang et al. |
| 7,446,882 | B2 | 11/2008 | DeLega et al. |
| 8,525,091 | B2 * | 9/2013 | Cui et al. .................. 250/201.9 |
| 2003/0053513 | A1 | 3/2003 | Vatan et al. |
| 2004/0184031 | A1 | 9/2004 | Vook et al. |
| 2006/0044988 | A1 | 3/2006 | Laborelli |
| 2006/0126336 | A1 | 6/2006 | Solomon |
| 2007/0121107 | A1 | 5/2007 | Tsai et al. |
| 2007/0188769 | A1 * | 8/2007 | Rohaly et al. ................ 356/602 |
| 2007/0201033 | A1 * | 8/2007 | Desjardins et al. ........... 356/497 |
| 2007/0280626 | A1 | 12/2007 | Haddock et al. |
| 2008/0100850 | A1 * | 5/2008 | Watson ........................ 356/601 |
| 2008/0131023 | A1 * | 6/2008 | Dowski et al. ................ 382/279 |
| 2008/0204729 | A1 * | 8/2008 | Manger et al. ................ 356/127 |
| 2009/0040602 | A1 | 2/2009 | Spilman et al. |
| 2011/0267508 | A1 * | 11/2011 | Kane et al. ................... 348/241 |
| 2013/0114085 | A1 * | 5/2013 | Wang et al. .................. 356/445 |

OTHER PUBLICATIONS

Muarkus C. Knauer et al , "Phase Measuring Deflectometry: a New Approach to Measure Specular Free-Form Surfaces", Proc. SPIE 5457, Optical Metrology in Production Engineering, 366 (Sep. 10, 2004).

S Bradbury et al., "Polarized light techniques". in Contrast Techniques in Light Microscopy, Microscopy Handbook Series 34,Jan. 1, 1996, pp. 49-58 (1996). BIOS Scientific Publishers, Ltd., Oxford, United Kingdom.

* cited by examiner

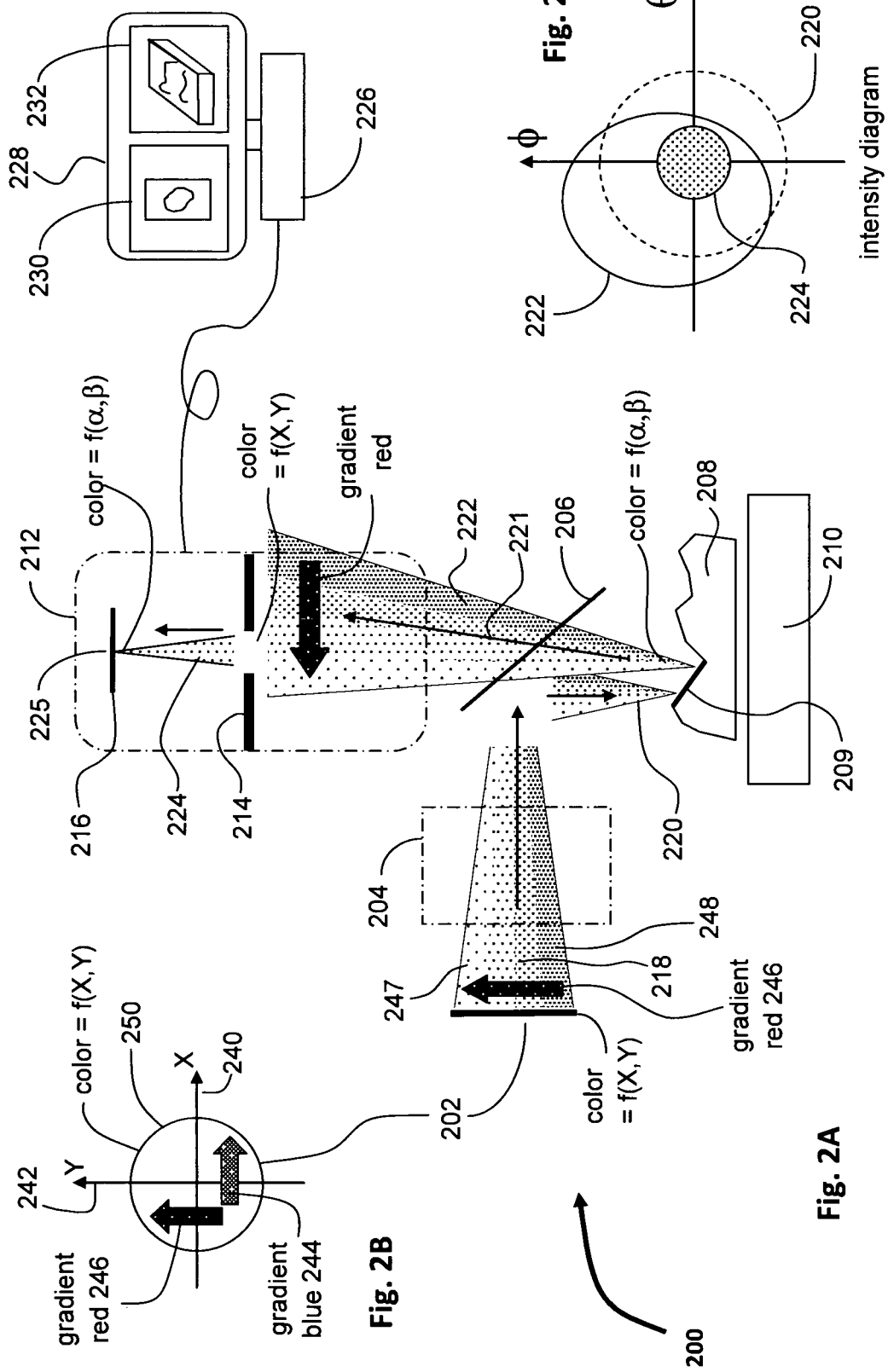

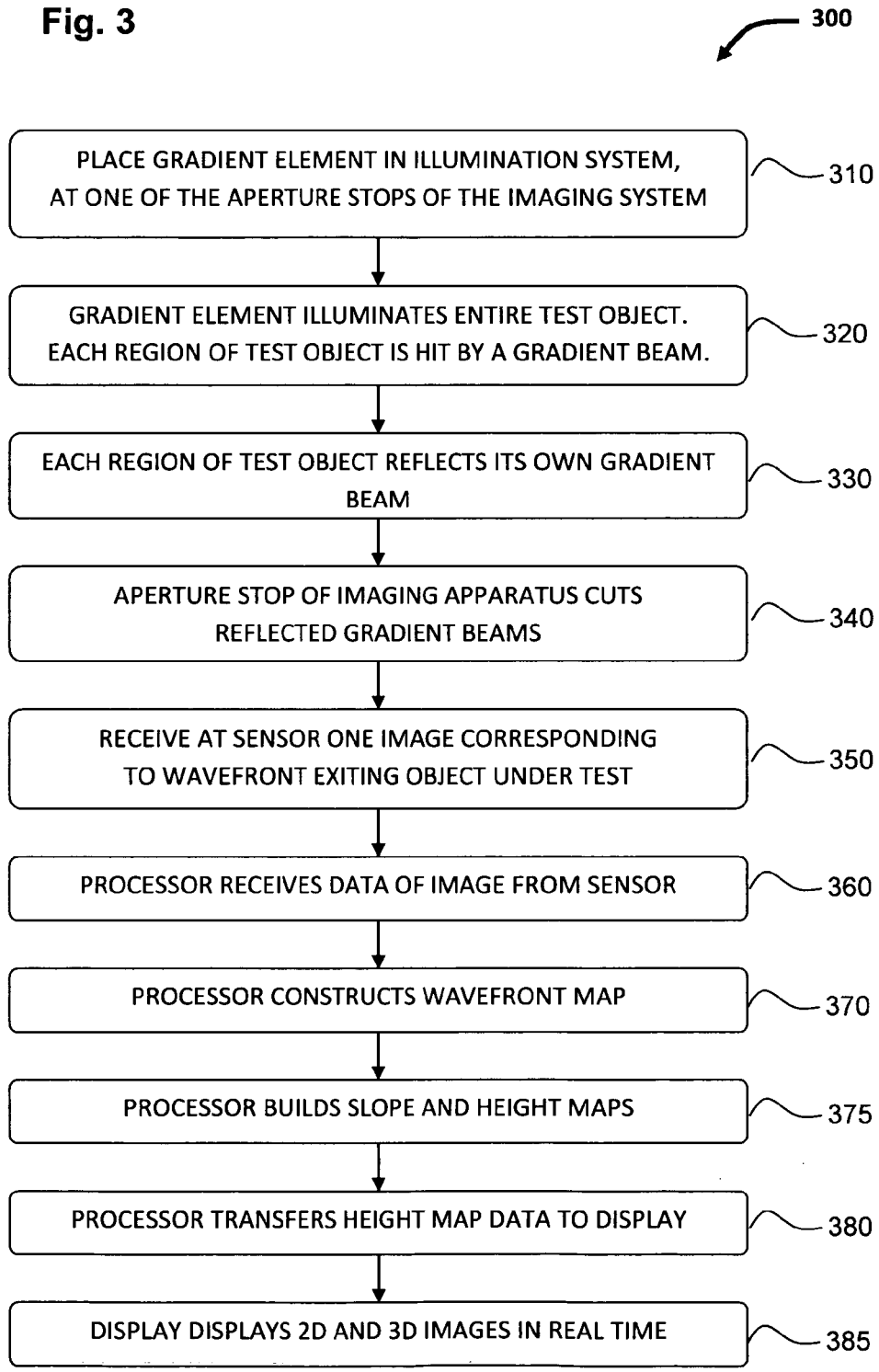

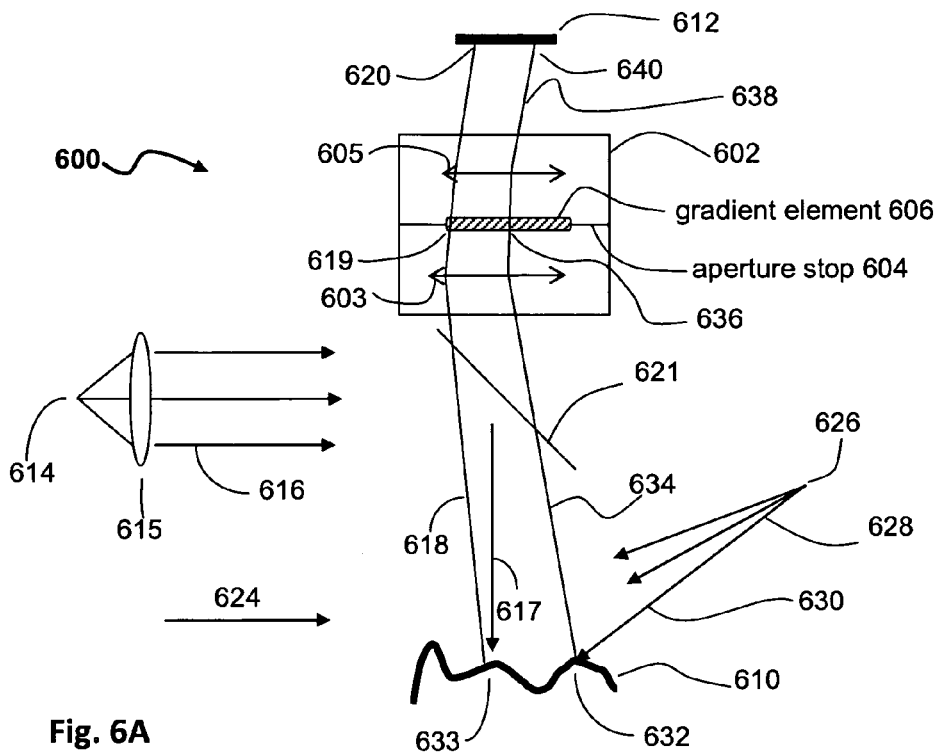
Fig. 6A
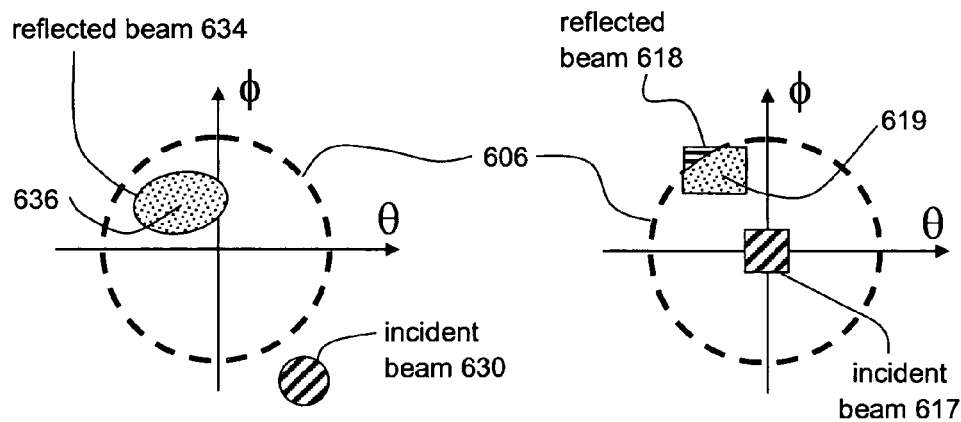
Fig. 6B  Fig. 6C
intensity diagrams

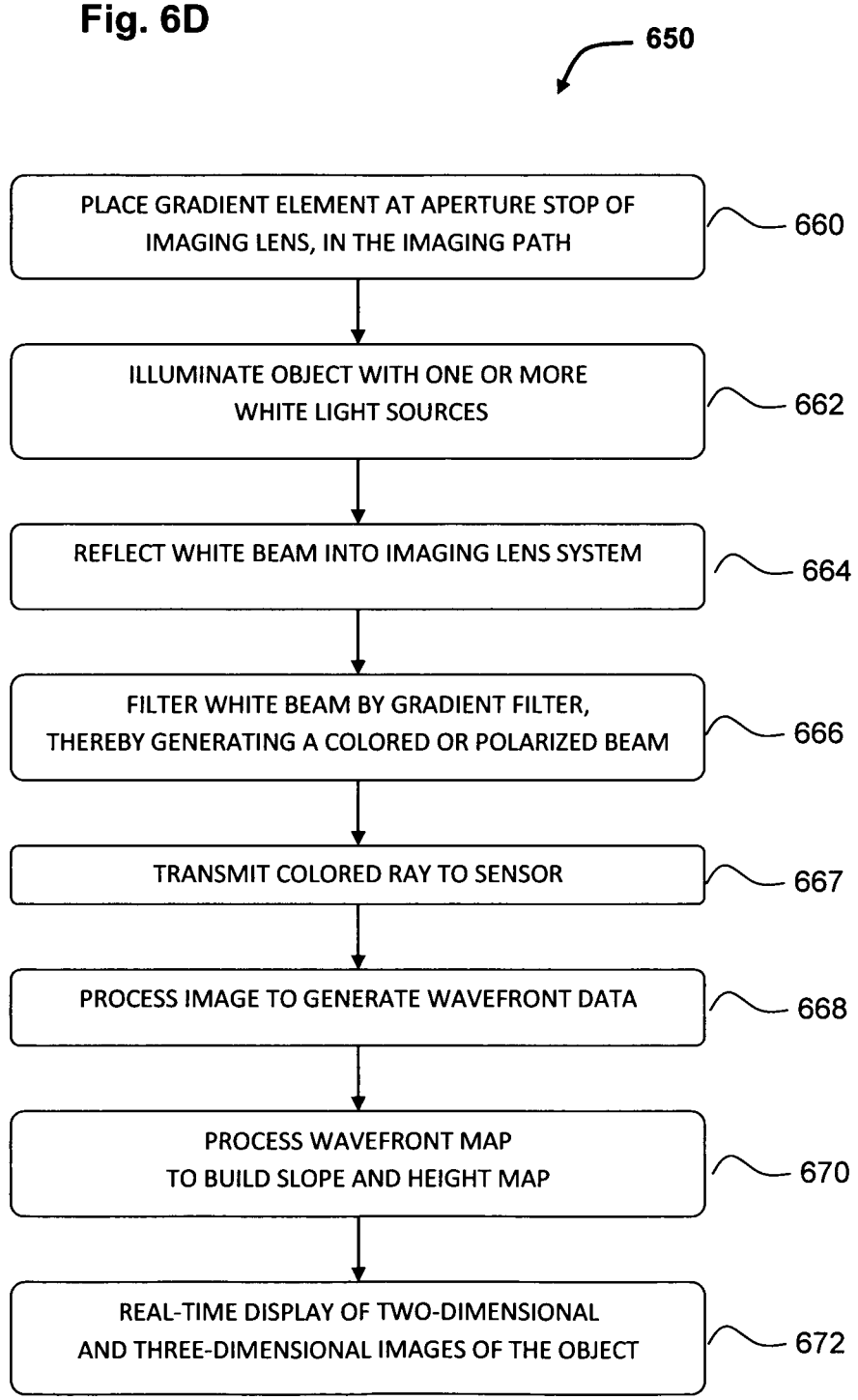

WAVEFRONT ANALYSIS INSPECTION APPARATUS AND METHOD

CROSS-REFERENCE TO RELATED APPLICATIONS

The current application is a U.S. National Phase Application under 35 U.S.C. 371 of PCT International Application No. PCT/IL2010/000177, which has an international filing date of Mar. 3, 2010, and which claims the benefit of priority from U.S. Provisional Patent Application No. 61/202,496, filed Mar. 4, 2009, and U.S. Provisional Patent Application No. 61/292,168, filed Jan. 5, 2010, the disclosures of which applications are incorporated herein by reference in their entirety.

FIELD OF THE INVENTION

The present invention relates generally to methods and apparatus for improved wavefront analysis for object inspection, applicable in both transmission and reflection modes, for respectively transparent and specular objects. Inspection may include metrology, 2D and 3D measurement, automated and visual inspection, detection, analysis, and quality control.

BACKGROUND OF THE INVENTION

In optical inspection technology, complex structures are inspected. This is the case for example in the semiconductor industry for the optical inspection of PCBs and wafers, and in the optics industry for the inspection of optical elements. Many inspection technologies exist, with 2D as well as with 3D capabilities. The chosen technology depends among others on the type of object and the type of searched information.

Some representative patent publications in the field include:

U.S. Pat. No. 6,556,706, to Geng, describes a three-dimensional imaging method and system illuminating an object to be imaged with a light pattern that is formed from two or more light sub-patterns. The sub-patterns can each encompass the visible light spectrum or can be spatially varying intensity sub-patterns that each correspond to a red, green, or blue component. The light pattern is generated by a slotted planar member or an optical filter. It should be noted that the system of '706 is not suitable for inspection and measurement of specular surfaces.

U.S. Pat. No. 5,825,476 to Abitbol et al., based on Hartman-Shack wavefront analysis method for transparent and specular objects, describes an apparatus for mapping an optical element. The teachings of Abitbol et al., comprises systems with low spatial resolution. Such systems are designed to measure dispersed sample points on the object under test and cannot be used to inspect objects continuously along their surface.

US 20060044988 to Laborelli, describes equipment for the optical playback of sound media which includes resources that have engraved grooves, for generating at least one light beam that presents a light spectrum variation according to its incidence angle on an area of the sound media and an image sensor placed so that it recovers the light reflected by said area of the sound media. This invention, applicable to specular surfaces, is limited in the shape of the measured area (line) and in its dimensions (same order of magnitude as the light source). Moreover, each point of the tested object sees a slightly different angular distribution.

US2004184031 discloses a three-dimensional optical inspection system, which reconstructs a three-dimensional image of the shape of the surface of an at least partially specular object resident on a printed circuit board by capturing two or more two-dimensional images of the object under different illumination configurations. The diffuse reflection, as well as the specular reflection can be used to reconstruct the three-dimensional image using any reconstruction method, such as photometric stereo. The different illumination configurations can be achieved using an illumination source including light-emitting elements arranged in concentric circular arrays, in which each of the circular arrays is divided into sections. Each section is independently controlled to selectively activate the sections to illuminate the object in a pre-established illumination pattern. The systems taught in '031 are limited in that they require a very large number of illumination sources and that there are dark regions dispersed between the illumination sources leading to "only a few discrete values of surface tilt". Moreover, each point of the tested object sees a slightly different angular distribution, which adds uncertainty to the height measurement.

There is still a need to provide improved optical systems for surface metrology, having the advantages of the cited publications altogether, without their limitations.

SUMMARY OF THE INVENTION

It is an object of some aspects of the present invention to provide optical systems and methods for the detection and measurements of objects.

It is an object of some aspects of the present invention to provide improved optical systems and methods for the detection and measurements of generally specular surfaces.

It is another object of some aspects of the present invention to provide improved optical systems and methods for the analysis of wavefront traversing transparent objects.

It is another object of some aspects of the present invention to provide improved optical systems allowing bright field illumination without the use of beam splitters.

In some embodiments of the present invention, improved methods and apparatus are provided for wavefront analysis inspection.

In other embodiments of the present invention, a method and system is described for providing improved inspection of specular objects.

There is thus provided according to an embodiment of the present invention, a wavefront analysis apparatus for optical inspection of an object, the apparatus including;
 a. at least one illumination system;
 b. at least one imaging system, constructed and configured to image the object onto an image plane;
 c. at least one gradient element disposed at least one of;
  i. an aperture stop of the at least one imaging system; and
  ii. a conjugate of the aperture stop of the at least one imaging system; and
 d. at least one sensor placed in an image plane of the at least one imaging system, wherein the at least one sensor is capable of differentiating between different areas of the gradient element thereby being adapted to provide data for calculation of optical properties of the object.

Further, according to an embodiment of the present invention, the at least one sensor includes at least one area sensor.

Additionally, according to an embodiment of the present invention, the at least one sensor includes at least one line sensor for scanning the object.

Moreover, according to an embodiment of the present invention, the at least one sensor includes at least one single cell sensor.

Yet further, according to an embodiment of the present invention, the apparatus is adapted for optical inspection using at least one human eye.

According to an embodiment of the present invention, each point of the object under test receives a similar angular distribution of light from the at least one illumination system.

Further, according to an embodiment of the present invention, each point of the object under test receives an identical angular distribution of light from the at least one illumination system, independent of a lateral position and a height position of the point.

Yet further, according to an embodiment of the present invention, the light source of the at least one illumination system is placed in at least one of a physical aperture stop plane of the at least one imaging system.

In some cases, according to an embodiment of the present invention, in the at least one illumination system includes at least two light sources.

Additionally, according to an embodiment of the present invention, an imaging lens in the at least one imaging system is an object-space telecentric lens.

Furthermore, according to an embodiment of the present invention, the at least one gradient element is disposed in the at least one illumination system.

Further, according to an embodiment of the present invention, the at least one gradient element is disposed in the at least one imaging system.

Yet further, according to an embodiment of the present invention, the at least one gradient element includes at least one discrete pattern gradient element.

Moreover, according to an embodiment of the present invention, the at least one gradient element includes at least one continuously varying gradient element.

Further, according to an embodiment of the present invention, the at least one gradient element each includes a plurality of regions, each region having unique characteristics.

Additionally, according to an embodiment of the present invention, the at least one gradient element each includes a plurality of regions, each region having a gradient of colors.

Further, according to an embodiment of the present invention, the at least one gradient element each includes a plurality of regions, each region having different time properties.

According to an embodiment of the present invention, the at least one gradient element each includes a plurality of regions, each region having a polarization state.

Furthermore, according to an embodiment of the present invention, the at least one gradient element includes at least one passive filter.

According to some embodiments, the wavefront analysis apparatus further includes a processor.

Further, according to an embodiment of the present invention, the processor is further constructed and configured to provide three dimensional data of the object.

Furthermore, according to an embodiment of the present invention, the processor is further constructed and configured to provide slope data of the object.

Additionally, according to an embodiment of the present invention, the processor is further constructed and configured to provide absolute height data of the object.

Yet further, according to an embodiment of the present invention, the processor is adapted to perform optical inspection of the object in real time.

According to an embodiment of the present invention, the at least one imaging system is configured to receive reflected light from the object.

Further, according to an embodiment of the present invention, the at least one imaging system is configured to receive transmitted light from the object.

Furthermore, according to an embodiment of the present invention, the apparatus includes at least one specular object inspection system and at least one diffuse object inspection system.

There is thus provided according to another embodiment of the present invention, an imaging system including at least one gradient element disposed in an at least one aperture stop thereof, the apparatus being constructed and configured to image an object onto an image plane.

There is thus provided according to yet another embodiment of the present invention, an optical system including at least one illumination system and at least one imaging system, wherein the at least one illumination system includes at least one active gradient element disposed in an aperture stop of the at least one imaging system.

Furthermore, according to an embodiment of the present invention, the at least one active gradient element is a spatial light modulator.

Further, according to an embodiment of the present invention, the at least one active gradient element includes an array of light emitting diodes (LEDs).

Yet further, according to an embodiment of the present invention, the at least one active gradient element includes an array of organic light emitting diodes (OLEDs).

Additionally, according to an embodiment of the present invention, the at least one active gradient element includes a scanning laser.

There is thus provided according to another embodiment of the present invention, a discrete active gradient light source including at least two light guides which enable passage of light from a first end to a second end thereof, wherein the first end includes at least one solid state light source and the second end is configured to be disposed at an aperture stop of an imaging system.

There is thus provided according to a further embodiment of the present invention An auto-illuminator optical system including;

a) an imaging system including at least one lens constructed and configured to image an object onto an image plane;

b) a light source placed in a physical aperture stop plane of the imaging system, the light source constructed and configured to illuminate the object;

wherein the light source is constructed and configured to allow at least some light reflected from the object to reach a sensor in the imaging system via the physical aperture stop plane.

Additionally, according to an embodiment of the present invention, the light source is in a clear aperture in the physical aperture stop plane; and wherein the at least some light reflected from the object forms an envelope around the light source.

Moreover, according to an embodiment of the present invention, the light source is in a clear aperture in the physical aperture stop plane.

Additionally, according to an embodiment of the present invention, the wavefront analysis apparatus may further include an auto-illuminator optical system as described herein.

There is thus provided according to another embodiment of the present invention, a method for producing an integrated light source including a solid state light source disposed on a substrate, the method including;

a) attaching the solid state light source on the substrate to form an integrated light element; and b) placing the integrated light element in an aperture stop of an imaging apparatus thereby forming the integrated light source, wherein the integrated light element is constructed and configured to enable light transmission at least partially from the aperture stop in a first direction and to further enable transmission of light reflected from an object under inspection in a second opposite direction through the aperture stop.

Additionally, according to an embodiment of the present invention, the substrate is a transparent substrate, and wherein the reflected light is through the transparent substrate.

A method for producing an integrated light source including a secondary light source, the method including:

a) introducing a primary light to a first end of a light guide; and b) placing a second end of the light guide in an aperture stop of an imaging apparatus thereby forming the integrated light source, wherein the integrated light source is constructed and configured to enable light transmission at least partially from the aperture stop in a first direction and to further enable transmission of light reflected from an object under inspection in a second opposite direction through the aperture stop.

A method for producing an integrated light source including a secondary light source, the method including:

a) introducing a mirror receiving light from a primary light source; and b) placing the mirror at an aperture stop of an imaging apparatus thereby forming the integrated light source, wherein the integrated light source is constructed and configured to enable light transmission at least partially from the aperture stop in a first direction and to further enable transmission of light reflected from an object under inspection in a second opposite direction through the aperture stop.

Additionally, according to an embodiment of the present invention, the system or apparatus of the present invention comprises at least one lens including at least one telecentric lens.

Additionally, according to an embodiment of the present invention, the at least one lens includes at least one zoom lens.

Additionally, according to an embodiment of the present invention, the system is adapted for use in endoscopy.

The present invention will be more fully understood from the following detailed description of the embodiments thereof, taken together with the drawings.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A is a simplified pictorial illustration of ray diagram of a first prior art having a Köhler illumination and a telecentric lens system in transmission mode;

FIG. 1B is a simplified pictorial illustration of prior art color filters;

FIG. 1C is a simplified pictorial illustration of a prior art bright field illumination imaging system;

FIG. 2A is a schematic pictorial illustration of a gradient surface inspection system in a reflection mode, according to an embodiment of the invention;

FIG. 2B is a simplified illustration of a gradient element of the system of FIG. 2A, according to an embodiment of the invention;

FIG. 2C is a simplified intensity diagram of beams of the system of FIG. 2A, according to an embodiment of the invention;

FIG. 3 is a simplified flow chart of a method for surface inspection, according to an embodiment of the invention;

FIG. 4 is a simplified pictorial illustration of a ray diagram from a gradient inspection system in transmission mode, with a gradient element disposed in the illumination path, in a plane conjugate with the aperture stop of the imaging apparatus, in accordance with an embodiment of the present invention;

FIG. 5A is a simplified pictorial illustration of a ray diagram from a gradient inspection system in reflection mode, with a gradient element disposed in the illumination path, in a plane conjugate with the aperture stop of the imaging apparatus, in accordance with an embodiment of the present invention;

FIG. 5B is a simplified illustration of a spatial distribution of a gradient element of the system of FIG. 5A, according to an embodiment of the invention;

FIG. 5C is an image of an object received by a sensor in the system of FIG. 5A;

Figure 7:
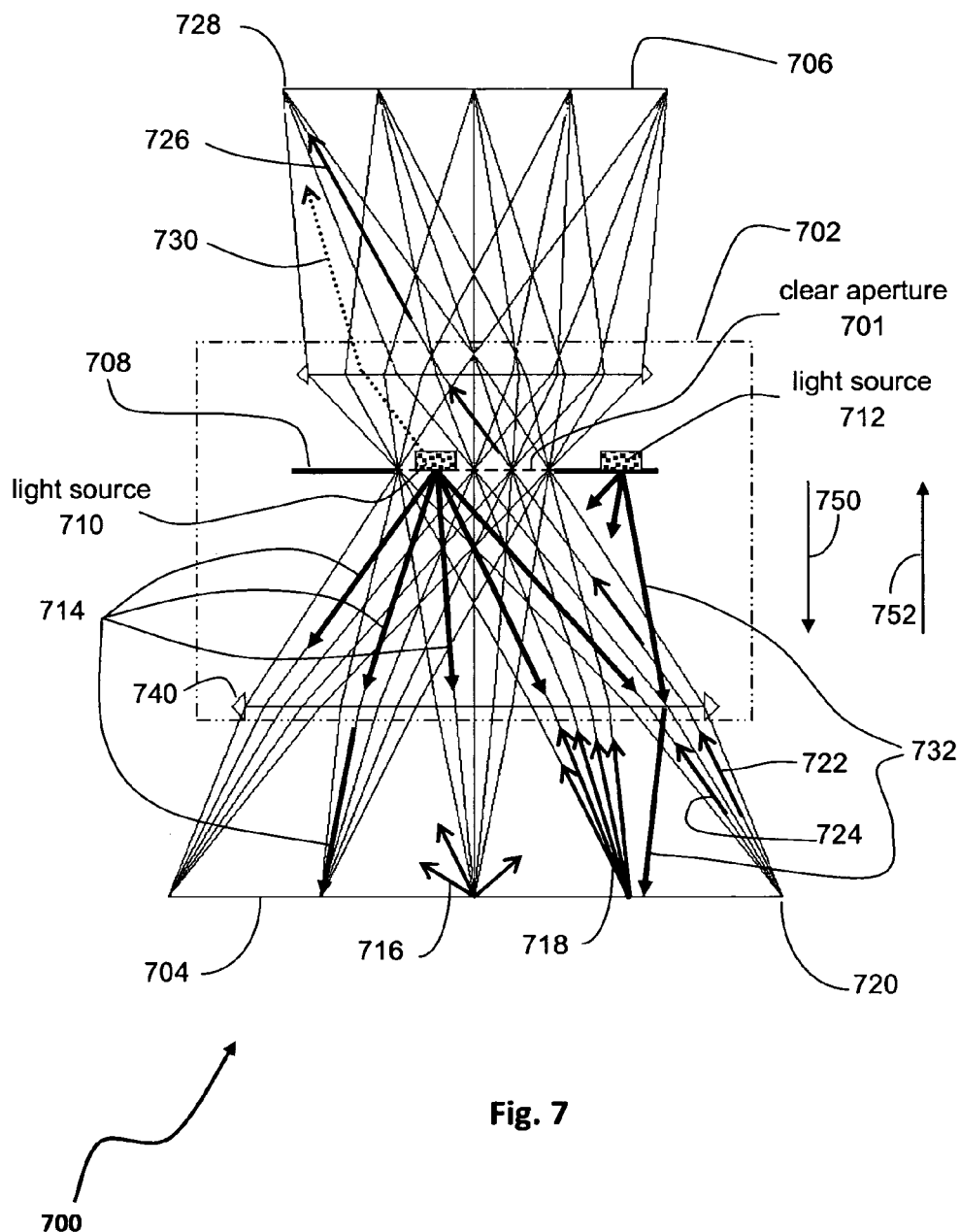
Figure 8:
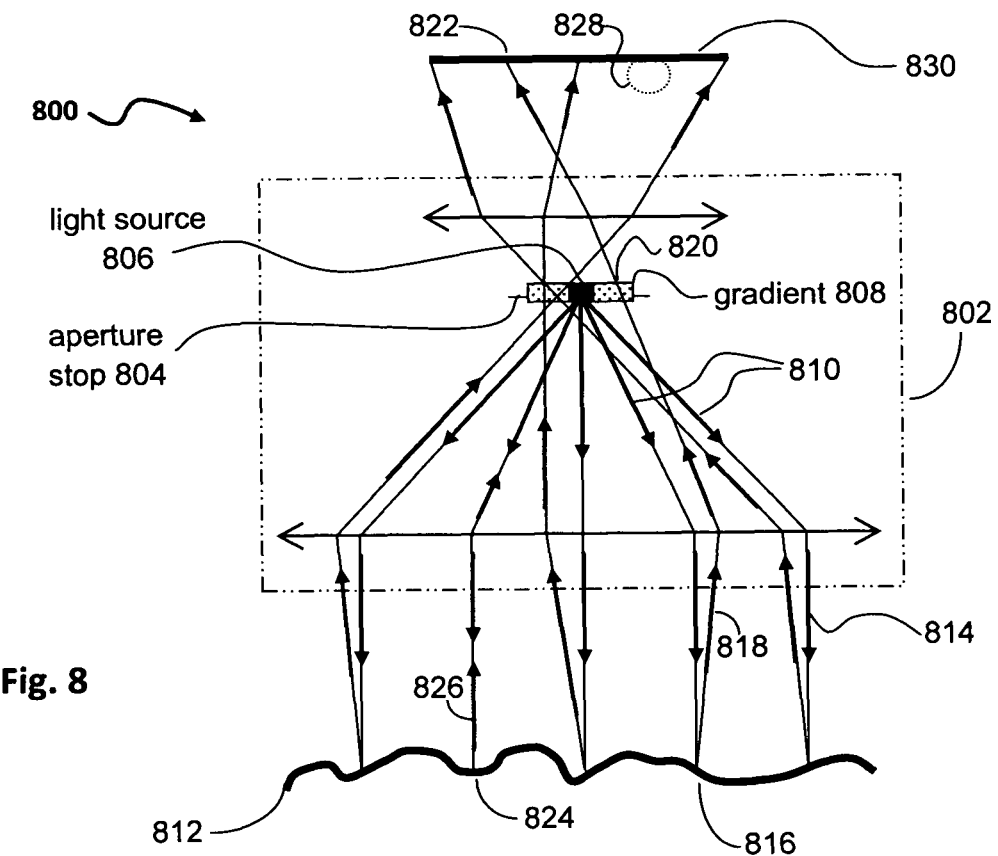
Figure 9A:
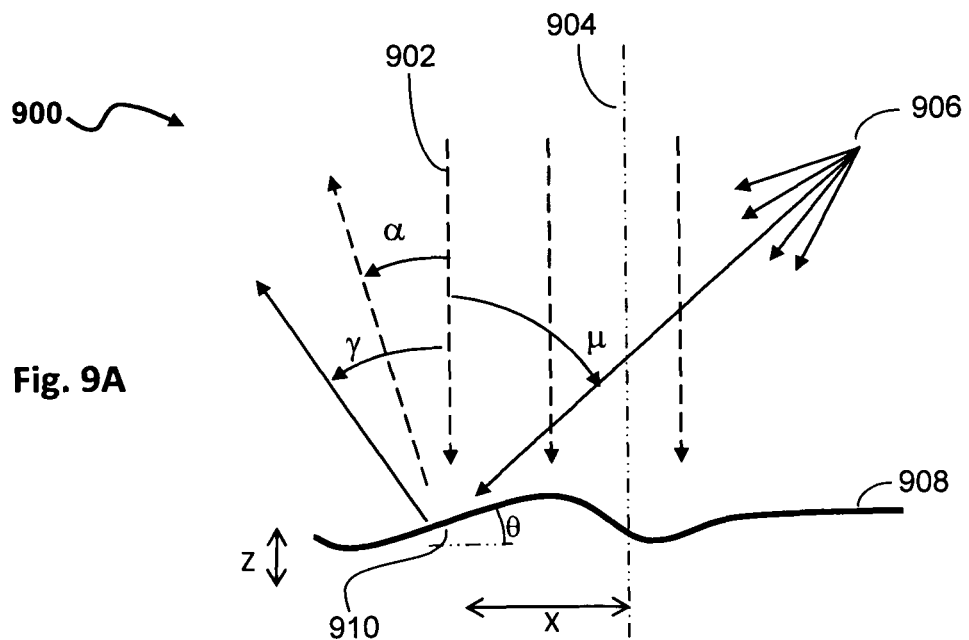
Figure 9B:
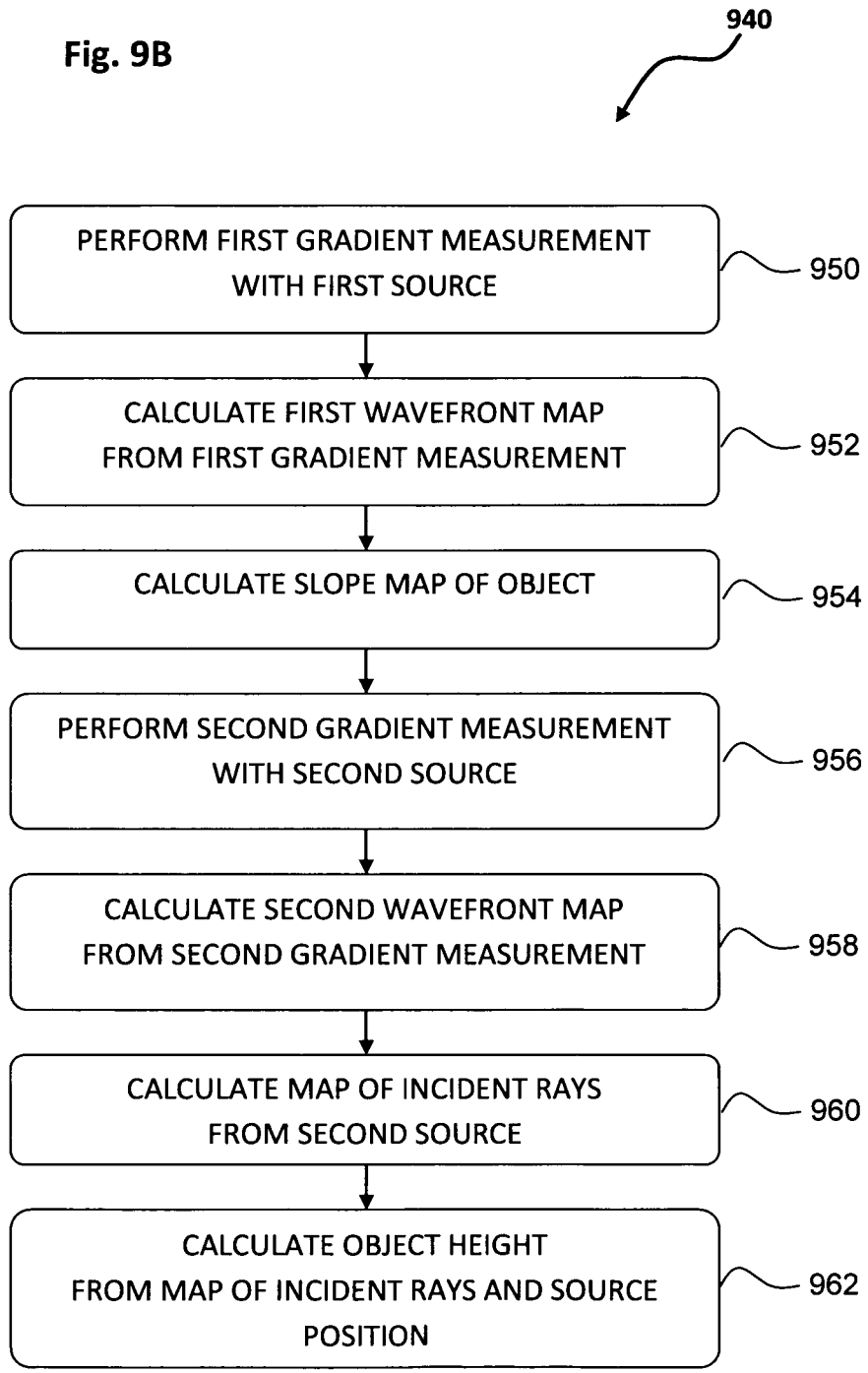
Figure 10:
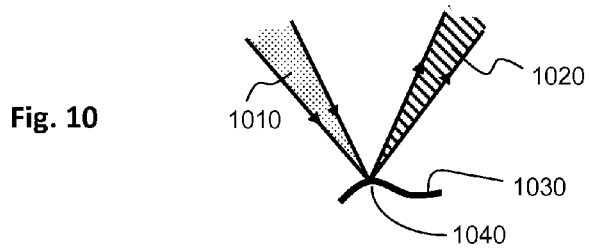
Figure 11:
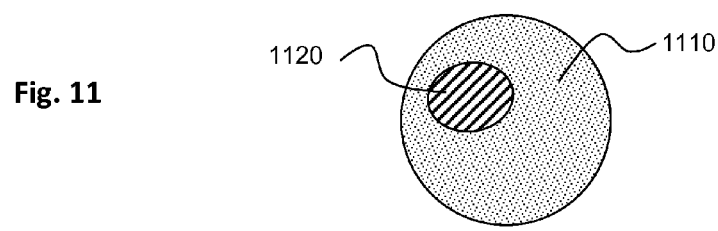
Figure 12A:
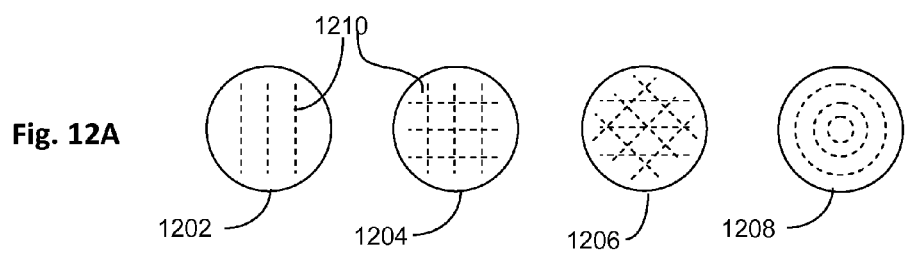
Figure 12B:
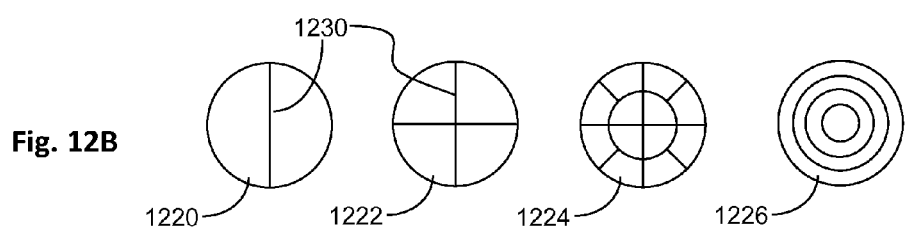
Figure 12C:
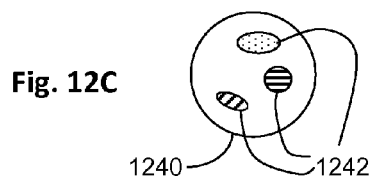
Figure 12D:
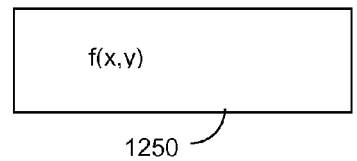
Figure 13:
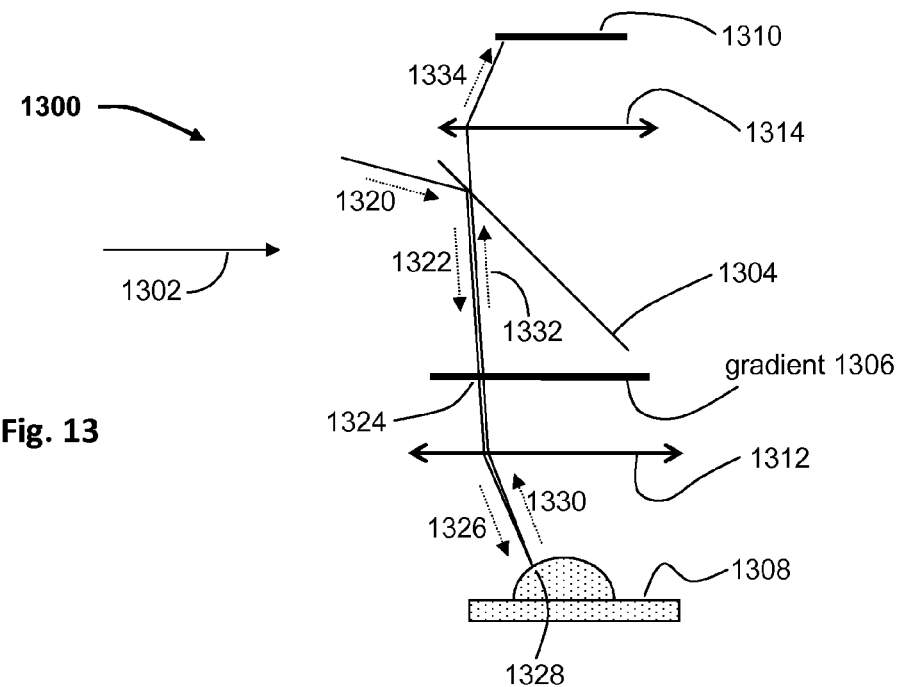
Figure 14:
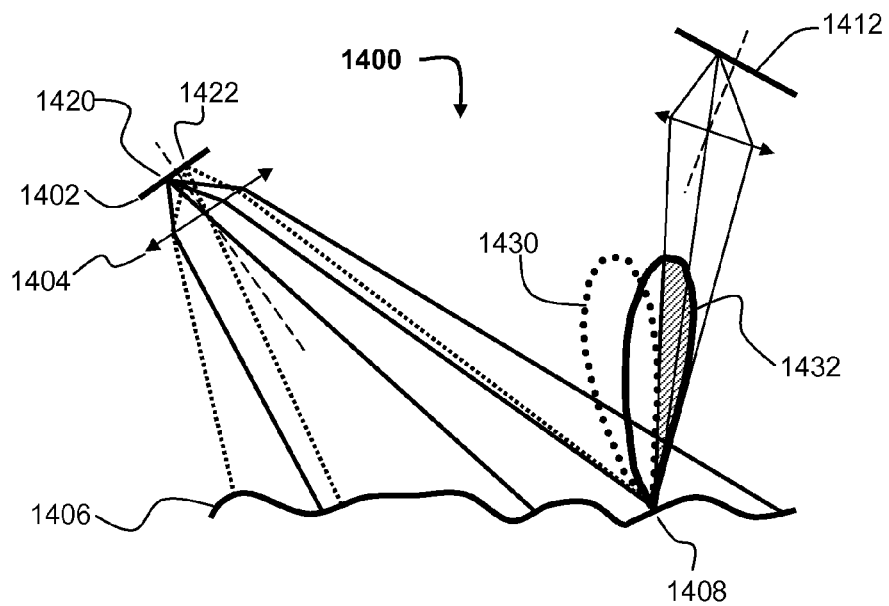
Figure 15:
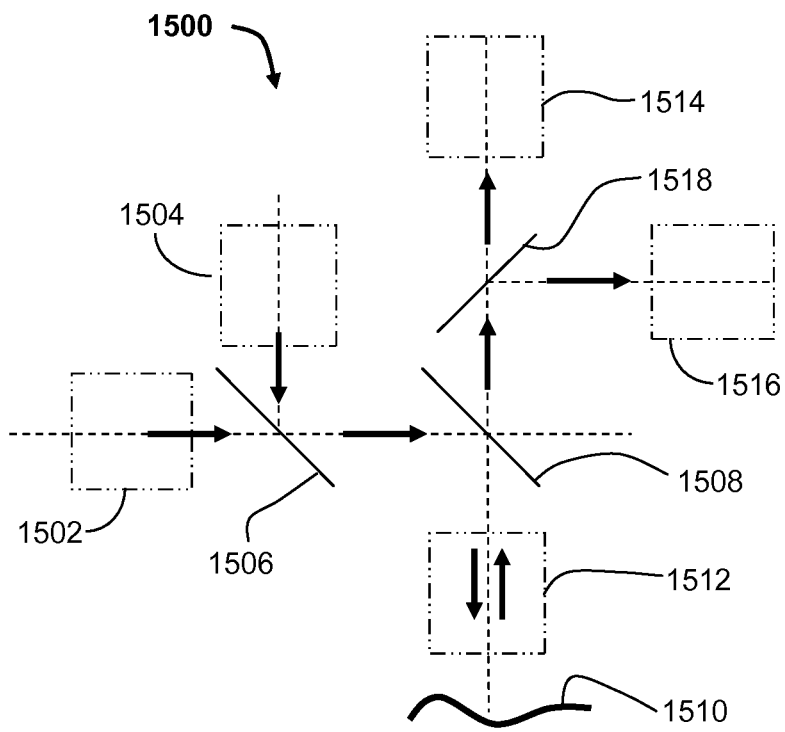
Figure 16:
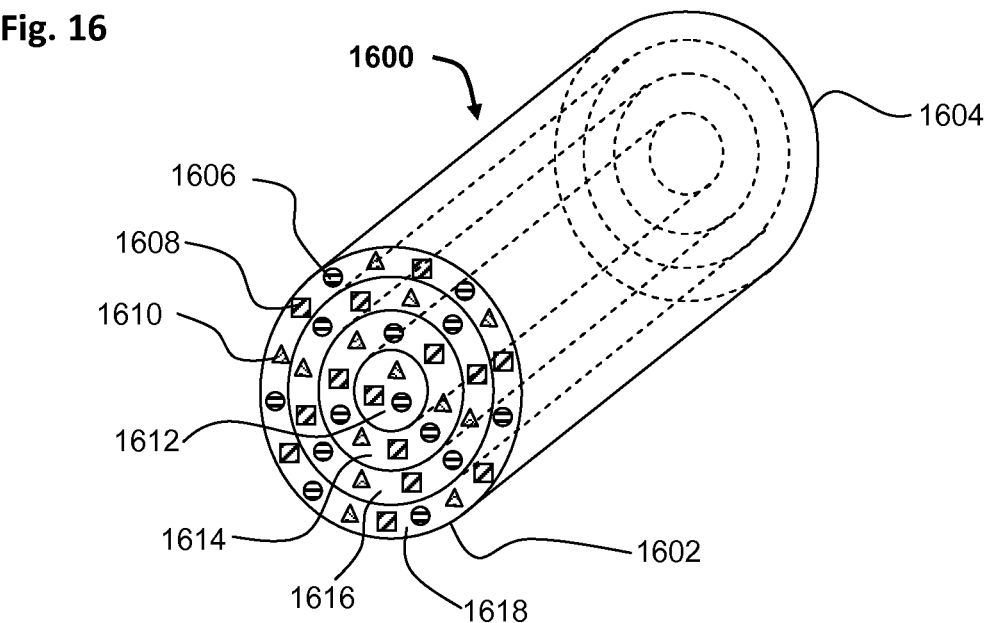

FIG. 6A is a simplified pictorial illustration of a gradient inspection system with a gradient element disposed in the imaging path, according to an embodiment of the present invention;

FIG. 6B is an intensity diagram of an incident beam and a reflected beam from the object surface in the system of FIG. 6A;

FIG. 6C is another intensity diagram of an incident beam and a reflected beam from the object surface in the system of FIG. 6A;

FIG. 6D is a simplified flow chart of a method for surface inspection using the system of FIG. 6A, according to an embodiment of the invention;

FIG. 7 is a simplified pictorial illustration of an auto-illuminator imaging system with integrated light sources disposed in one of its physical aperture stop planes, according to an embodiment of the present invention;

FIG. 8 is a simplified pictorial illustration of an auto-illuminator gradient inspection system, having a telecentric imaging system with a light source and gradient element disposed in one of its aperture stop planes, according to an embodiment of the present invention;

FIG. 9A is a simplified pictorial representation of a step measuring methodology using the gradient elements of the present invention;

FIG. 9B is a simplified flow chart of a step measuring methodology using the gradient elements of the present invention;

FIG. 10 is a simplified pictorial illustration of the angular extent of rays impinging a specular object and reflected back, according to an embodiment of the present invention;

FIG. 11 is a synthesis of intensity diagrams, illustrating the calculation of received beams;

FIG. 12A shows simplified pictorial illustrations of gradient elements with continuously varying gradient patterns, according to some embodiments of the present invention;

FIG. 12B shows simplified pictorial illustrations of gradient elements with discrete gradient patterns, according to some embodiments of the present invention;

FIG. 12C shows simplified pictorial illustrations of a gradient element with discrete gradient patterns for identification of known object signatures, according to some embodiments of the present invention;

FIG. 12D shows a schematic pictorial illustration of a rectangular gradient element to be placed in the illumination path of line scanning systems, according to some embodiments of the present invention;

FIG. 13 is a simplified pictorial illustration of a ray diagram of a gradient inspection system in reflection mode, according to an embodiment of the present invention;

FIG. 14 is a simplified pictorial illustration of a ray diagram in a general case of a gradient inspection system in a reflection mode, according to an embodiment of the present invention;

FIG. 15 is a simplified illustration of a general setup of a gradient inspection system for use in calibration, superimposition of images and analysis of complex surfaces, according to an embodiment of the present invention; and FIG. 16 is a schematic pictorial illustration of an example of an active discrete gradient light source built with light guides.

In all the figures similar reference numerals identify similar parts.

DETAILED DESCRIPTION OF PREFERRED EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

There are many types of wavefront sensors operative by means of interferometry, Moiré, Hartmann-Shack and others. Some of these are difficult to implement, are sensitive to their environment, have limited resolution and others work better with certain types of surfaces. In this invention, the term "inspection systems" includes, among others, visual and automated inspection, 3D metrology, quality control, measurement, analysis and detection of objects, patterns and defects.

"Spectrum" is defined as a collection of wavelengths at their respective relative powers, typically within the range UV to IR, although other forms of radiation and other wavelengths may be used where appropriate.

Specular reflection is mirror-like reflection of light from a surface, in which light from a single incoming direction (a ray) is reflected into a single outgoing direction. Such behavior is described by the law of reflection, which states that the direction of incoming light (the incident ray), and the direction of outgoing reflected light (the reflected ray) make the same angle with respect to the surface normal, thus the angle of incidence equals the angle of reflection.

As opposed to specular reflection, there is Lambertian reflection, in which the ray is diffused into all directions. There are also Gaussian reflections, in which the ray is reflected towards a preferred direction, but with a Gaussian distribution. Surfaces may have a composite behavior, exhibiting all these types of reflections.

A specular surface is defined herein to mean a surface whose reflected beam has a strong specular component at a given spectrum, other parts of the light may be diffused, absorbed and transmitted.

A transparent object is an object capable of transmitting light. The transmitted wavefront may be distorted after passage through the transparent object. Some other parts of the incident light may be absorbed, diffused and back-reflected.

Figure 4:
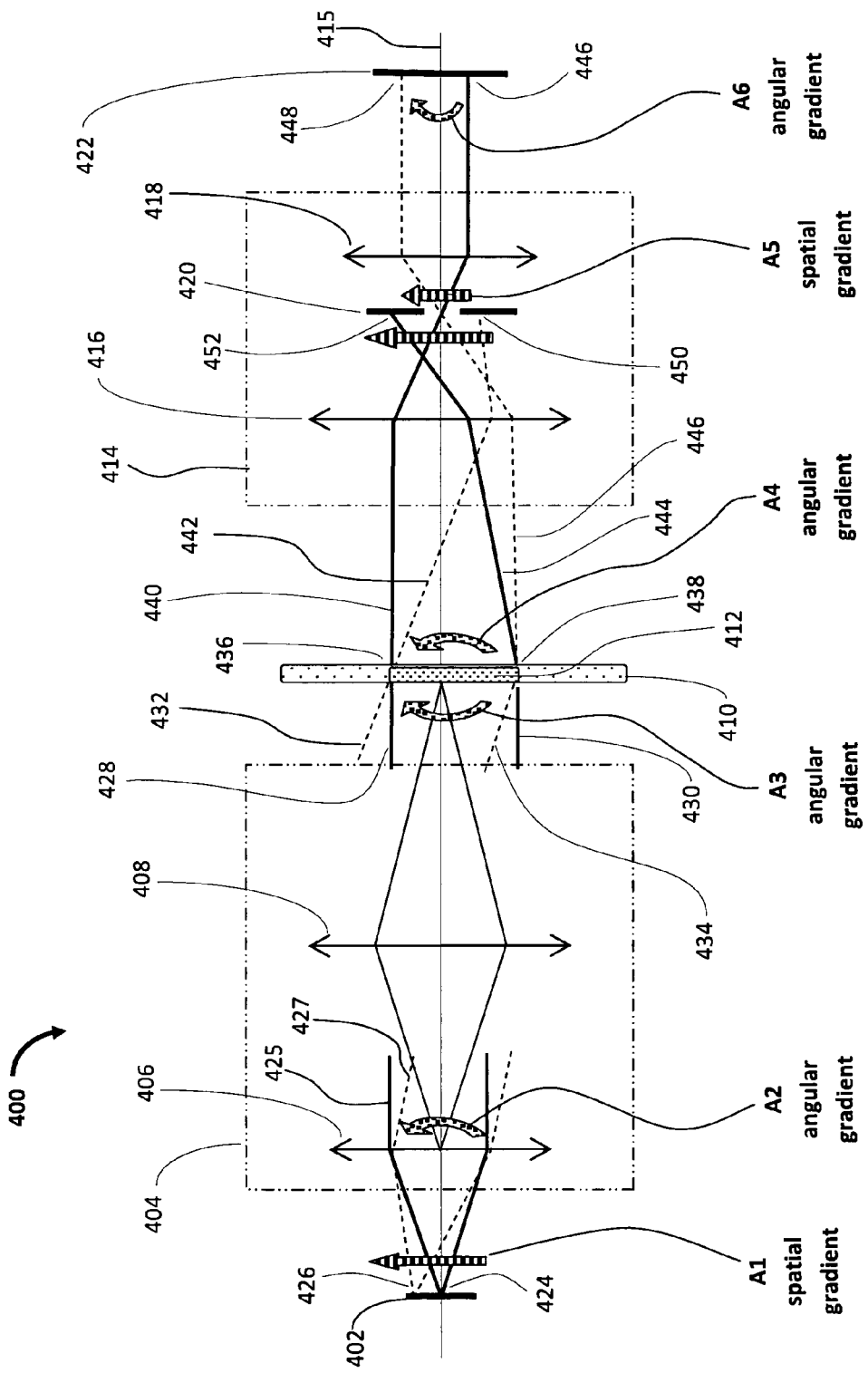

There are two major types of advanced illumination systems, namely critical and Köhler systems. In a critical system, the light source is imaged on the object to be illuminated, such that each point of the source becomes an illuminated point on the object. In a Köhler illumination system, the far field is imaged on the object to be illuminated, such that each point of the source becomes a beam covering the entire surface under test, and each point of the surface under test sees rays coming from the entire effective surface of the source. One simple example is shown in FIG. 4, in which a light source 402 is placed at the focal plane of a lens 406. This lens may be further projected on the object to be illuminated. Köhler illumination is used in numerous optical instruments, such as microscopes and projectors, where the illumination uniformity is important.

A common method for three-dimensional measurement is the use of structured light, as for example in publication U.S. Pat. No. 6,556,706. A pattern is projected on an object, and a camera looks at this pattern from an angle different from the illumination. The deformed pattern helps reconstructing the 3D shape of the object. This method works well with diffusive surfaces.

The aperture stop of an optical system has several characteristics. One of them is that it is the spatial representation of the angular distribution of the object and image planes. As an illustration, in the case of an image-space telecentric lens, all the rays going through the same point on the aperture stop reach the entire image plane at the same incident orientation.

Two or more planes are called conjugates if they are images of each other through an optical system. In an optical inspection system comprising an illumination system and an imaging system, the imaging system is constructed and configured to image an object plane onto an image plane. The aperture stop of the imaging system may have several conjugates planes. "One of the aperture stops of the imaging system" means herein the aperture stop of the imaging system itself or one of its conjugates, as well in the imaging path as in the illumination path.

The present invention relates to uses of gradient elements, such as those shown in FIGS. 12A-D and used, inter alia, in the systems of FIGS. 2A, 4, 5A, 6A, 8 and 13. The gradient elements may be suitably disposed at one of the aperture stops of an imaging system of an inspection system. The gradient elements enable new inspection capabilities of these systems, as is elaborated hereinbelow.

A gradient element comprises at least two different areas, each area enabling passage of light of defined measurable characteristics therethrough, selected from spectrum, power, polarization and time. A gradient element may be, in some cases, an active light source or a passive component such as a filtering optical element (See FIGS. 12A-D for further details).

At least one sensor may be disposed in the image plane of one of the imaging systems, the sensor being constructed and configured to differentiate, either simultaneously or successively, between the areas of the gradient element. The sensor may be composed of one or a plurality of sensors, and may be for example a simple photodiode, a line sensor, a color image sensor, or the human eye.

A gradient inspection system is defined herein as an inspection system having at least one gradient element at one of the aperture stops of one of its imaging systems, and at least one sensor in the image plane of one of its imaging system, capable of differentiating between the areas of the gradient element.

An object under test may be placed in an object plane of the imaging system(s) or, alternatively, at another suitable position in the system.

A gradient inspection system of the present invention is constructed and configured to analyze the deflection of the illumination reaching the object under test by differentiation of the areas of the gradient element, and extracting information concerning the test object.

It is a particular feature of some of the embodiments of the current invention that a known incoming beam reaching the entire object under test is deflected in a different way by each point of said object. The beams imaging each point of said object onto the sensor receive the local characteristics of one or more areas of the gradient element, such that the received characteristics depend upon the deflection of these beams at those said points. The sensor captures those received characteristics for each point of the object. A straightforward image processing, simply translating a characteristics such as color and gray level into a slope, reconstructs the full wavefront in real time.

It is another particular feature of some of the embodiments of the current invention that the light source of an inspection system is disposed at one of the physical aperture stop planes of the imaging system. The light source is designed such that light coming back from the object towards the sensor can still be transmitted through the aperture stop.

Figure 1A:
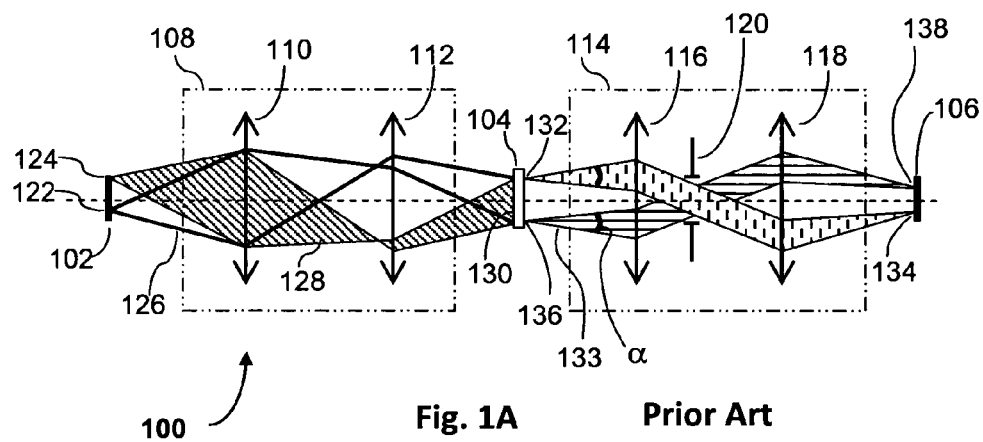

Turning to FIG. 1A, there is seen a simplified pictorial illustration of a ray diagram of an inspection system 100 in transmission mode, composed of a Köhler illumination 108 and a telecentric imaging system 114.

A light source 102 is placed at the source plane of a Köhler illumination apparatus 108, composed of one or more lenses or group of lenses 110, 112. In this current example, the lens or group of lenses 110 collects light from the light source 102, while the lens or group of lenses 112 images the lens or group of lenses 110 onto the object under test 104. Each point source 122, 124 belonging to the light source 102 creates a full beam 126, 128 and illuminates the same region 130 of object 104. The Köhler illumination apparatus 108 enables the uniform illumination of a large region of object 104.

An object-space telecentric lens imaging apparatus 114 images object 104 onto sensor 106. Apparatus 114 is made of at least two lenses or group of lenses 116 and 118 and of an aperture stop 120. Points 132, 136 of object 104 are imaged to points 134, 138 on sensor 106. The telecentric imaging apparatus 114 is designed to collect a generally collimated light from object 104, the aperture stop 120 controlling the angular extent a of the collected sub-beams 133 coming from each point of the object. It is noted that the light source 102 is placed in one of the conjugates of the aperture stop 120 of the imaging system 114. This prior art system 100 may be used in imaging systems, such as microscopes and machine vision systems, but, as is, cannot analyze wavefronts (in contrast to systems 200—FIG. 2A—and 400—FIG. 4—of the present invention).

Figure 1B:
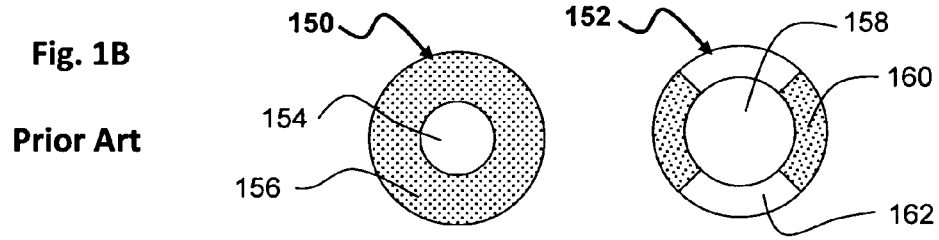

Some prior art systems, such as system 100, use color filters. FIG. 1B is a simplified pictorial illustration of prior art color filters 150, 152, sometimes called Rheinberg filters, which may be placed at a source plane 102 (FIG. 1A) in order to visually enhance image contrast. The inner rings 154, 158 correspond to bright field illumination, the outer rings 156, 160, 162 correspond to dark field illumination. Regions 154, 156, 158, 160, 162 are of a uniform color of any color. With these filters, bright and dark fields are well differentiated. These filters are used in microscopy systems in order to see the background in the color of the inner ring, and the edges of the transparent specimen in the color of the outer ring. However, the patterns of these prior art filters are only designed to enhance the visual contrast. The only information that may be extracted from the systems using these filters is whether the rays reaching the specimen came from the bright or the dark field. Such analysis is not performed because of the lack of interest in such information for the applications using this technique. These Rheinberg illuminations have not been used for wavefront analysis.

Figure 1C:
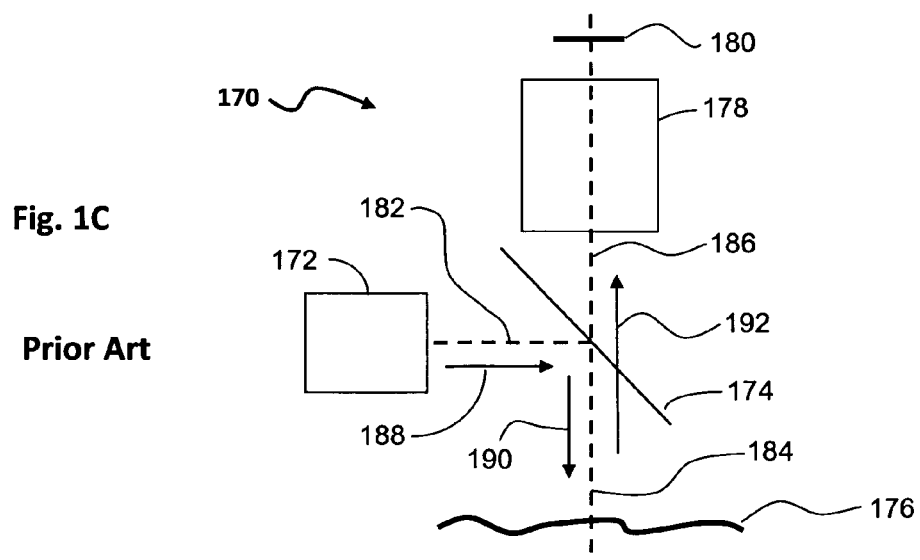

FIG. 1C is a simplified pictorial illustration of a prior art bright field illumination imaging system 170. An object under inspection 176 receives light from a light source 172 via a beam splitter 174. An imaging apparatus 178 comprises an imaging lens (not shown) and transfers an image of the object 176 to a sensor 180. An emitted beam 188 travels from light source 172 along illumination axis 182 to the beam splitter 174, where the beam is split along imaging axis 184. Incident beam 190 impinges on the object and a reflected beam 192 travels along imaging optical axis 184,186 to the imaging apparatus 178. The system 170 has the disadvantage of having a side arm (not shown) comprising light source 172. Moreover, the beam splitter extends the distance between the object 176 and the imaging apparatus 178, and the diameter of the optical elements constituting it, especially for high angles of illumination and/or imaging. The performances of the imaging apparatus 178 may also be reduced because of optical aberrations induced by the beam splitter.

System 170 requires beam splitter 174. Compared to an equivalent system with an off-axis illumination without beam splitter, the beam splitter reduces the quantity of energy reaching sensor 180. In a 50%-50% beam splitter, only 50% of the energy emitted by the source 172 reaches the object 176, and 50% of the energy reflected by object 176 is transmitted towards sensor 180. All-in-all, no more than 25% of the energy emitted by the light source 172 can reach the sensor 180.

There are many types of beam splitters (BS) such as plate BS (semi-reflective coating on window), cube BS (2 bonded prisms), dichroic BS (one spectrum is reflected, while another one is transmitted), polarizer BS, polka-dot BS (array of reflective dots on a window) and pellicle BS. Some of them cause energy losses by undesired reflections and absorption, thus preventing attainment of 50% efficiency.

Other prior art systems may be used for illuminating objects without a beam splitter, but are off-axis, which means that the illuminating beam has an optical axis different from that of the imaging beam. These systems are sometimes called "dark field". They can create shadows on the object. Moreover, the beam reflected by a specular region of the object misses an imaging system not placed symmetrically to the incoming beam in regards with the normal to such regions.

Reference is now made to FIG. 2A, which is a schematic pictorial illustration of a gradient surface inspection system 200, in reflection mode, according to an embodiment of the invention. The system has to be seen in 3D, although it is represented in 2D for easier understanding. System 200 is used to inspect an object 208. The method of using system 200 is described with respect to FIG. 3 hereinbelow.

System 200 comprises an illumination apparatus 204 and an imaging apparatus 212. Imaging apparatus is composed of an imaging system (not shown), an aperture stop 214 and a sensor 216. Imaging apparatus 212 is connected to a processor or computer 226 and display 228. Display 228 is constructed and configured to display a two dimensional image 230 and/or a three dimensional image 232 relating to object 208. Further details of the optics inside an illumination apparatus 204 and an imaging apparatus 212 are seen with respect to a transmission system shown in FIG. 4.

Object 208 may be placed on a suitable movable stage 210, which may be moved along one, two or three axes, as is known in the art. The movement of stage 210 may be controlled by system 200. Some exemplary forms of the illumination apparatus and imaging apparatus of the present invention are shown hereinbelow in FIGS. 4, 5A, 6A, 8, 13, 14 and 15.

FIG. 2B is a simplified illustration of gradient element 202 of the system of FIG. 2A, according to an embodiment of the invention.

Gradient element 202 comprises at least one color pattern disposed along a first axis, such as y axis 242 having a color red gradient 246. The red gradient comprises regions of low red intensity 247 and regions of high red intensity 248. Gradient element 202 may comprise additional patterns or color gradients, such as blue gradient 244 disposed along another axis, such as x axis 240. Gradient element 202 may have a circular cross section 250.

Red and blue linear gradients are given here as examples. The spatial configuration, meaning the color at each point X, Y of the gradient element, can be any configuration, and can be summarized by a function f(x, y).

In reflection mode, system 200 is used to image object 208 by means of Köhler illumination apparatus 204. The Köhler illumination apparatus is aimed to create a gradient beam 218, such that the angular distribution f(α, β) of gradient beam 218 corresponds to the spatial distribution f(x, y) of the gradient element 202. The gradient beam 218 impinges on a beam splitter 206. The beam splitter enables part of the incident gradient beam 220 to fall on a region 209 of the object. A reflected gradient beam 222 is reflected from region 209 towards an aperture stop 214 of an imaging apparatus 212. The aperture stop 214 may let only a part of the angular distribution of gradient beam 222 pass through it. The partial or cut gradient beam 224 may keep only some of the local characteristics of gradient beam 222. The part of the characteristics that are kept depends on the local slope of region 209. Said cut beam 224 is focused onto region 225 of sensor 216. The sensor is able to identify the local characteristics remaining in the cut beam 224. The sensor is connected to a computing system 226, able to translate any received local characteristics from any region 209 of object 208 into a slope at said regions 209. Computing system 226 comprises a display 228, adapted to display at least one of a two-dimensional display 230 and three-dimensional display 232.

It is noted that the gradient feature is in the spatial domain (color=f(x,y)) at the planes conjugate with the imaging apparatus aperture stop, e.g. Köhler focal plane and the aperture stop itself. The gradient feature is in the angular domain (color=f(α, β)) at the planes conjugate with the object under test, e.g. the object itself and the image plane of the imaging apparatus, i.e., sensor 216.

The gradient surface inspection system 200 is therefore able to measure the wavefront exiting the object 208, and to display a slope map of said object.

FIG. 2C is a simplified intensity diagram of beams 220, 222 and 224 of system 200 of FIG. 2A, according to an embodiment of the invention. This diagram provides qualitative data of angular distribution of beams 220, 222 and 224 over two perpendicular axes theta θ and phi Φ, both perpendicular to the optical axis (not shown) of the imaging apparatus 212. The incident gradient beam 220 impinges object 208 parallel to the optical axis. The reflected gradient beam 222 is deviated, said deviation depending on the local tilt of region 209. Reflected beam 222 may be deformed. The aperture stop cuts gradient beam 222, such that only the part parallel to the optical axis of the imaging apparatus is transmitted therethrough. Cut beam 224 keeps only some of the local characteristics of gradient beam 222.

FIG. 3 is a simplified flow chart 300 of a method for surface inspection, according to an embodiment of the invention. This methodology is exemplified with reference to the system 200 of FIG. 2A, but could be implemented with any of the systems described hereinbelow (possibly with minor method changes).

In a set-up step 310, a suitable gradient element 202 is placed in the focal plane of Köhler illumination 204, and is therefore at one of the conjugates of the imaging system aperture stop 214. The gradient element may be any suitable gradient element, such as gradient element 202 (FIG. 2A), 402 (FIG. 4), 502 (FIG. 5A), 606 (FIG. 6A), 808 (FIG. 8) or gradient elements 1202, 1204, 1206, 1208, 1220, 1222, 1224 and 1226 of FIGS. 12A-12C.

In an illuminating step 320, the gradient element illuminates entire test object 208 via Köhler illumination 204. Each region 209 of the object receives a gradient illumination beam 220 having gradient angular characteristics (color or other) corresponding to the gradient spatial pattern of the gradient element 202.

In a reflecting step 330, the topology/morphology and the surface state at each point 209 of the object determines the angular characteristics of each reflected gradient beam 222. The direction 221 of each beam 222 depends on the slope of each region 209.

In a cutting step 340, aperture stop 214 of imaging apparatus 212 cuts each reflected gradient beam 222 into cut gradient beam 224. The part of each reflected gradient beam 222 that is transmitted through the aperture stop depends on the direction 221 of said reflected beam 222. Therefore, the characteristics such as color of each cut beam 224 depend on the local slope at each region 209. The aperture stop cuts each gradient beam 222 to a limited angular extent, letting only part of each cut beam 224 focus and reach sensor 216.

In a receiving step 350, sensor 216 receives focused cut beams 224 at regions 225. Each region 225 is the image of a region 209 through the imaging system (not shown). Each region 225 has characteristics, such as color, which depend on the slope of the region 209 of object 208. Thus, the obtained image on the sensor is the image of the object under test, where each region (such as pixel) of the obtained image has characteristics (such as color or gray level) depending on the local slope of the corresponding region on the object. The obtained image is a color-coded map of the wavefront exiting the object.

In a first transmission step 360, processor 226 receives data of the obtained image from sensor 216. Thereafter, in a first construction step 370, processor 226 constructs a map of the wavefront exiting object 208 by corresponding each characteristics of the obtained image to a wavefront slope. In a second construction step 375, processor 226 constructs a slope map of the object from wavefront map and from data of the incident beam 220. A height map of continuous regions of the object may be constructed from the slope map.

In a transferring step 380, the processor transfers height map data to display 228. In a displaying step 385, the display displays in real time 2D and 3D images of the object under test, the 2D image being obtained using standard means known in the art.

As can be understood from FIGS. 2A-3, the system of the present invention enables enhanced optical inspection of specular and transparent objects using wavefront analysis technique, with the following advantages:

a. The gradient elements of the present invention can be cheaply implemented into existing imaging systems, such as microscopes and line scanning systems. Numerous standardized existing prior art 2D imaging systems can be easily upgraded into 3D measuring systems by the simple addition of a single gradient element.

b. The spatial resolution of the present invention is limited by the one of the imaging apparatus (mainly pixel size and MTF), thus providing the highest spatial resolution available today.

c. The slope resolution is limited by the dynamic range of the sensor, usually 8 to 10 bits (256 to 1024 levels).

d. The systems of the present invention have a low sensitivity to environment, as opposed to interferometry-based systems that may have equivalent performances to the present invention.

e. The systems of the present invention may require only one or sometimes two images (the second one for color calibration, as will be explained in FIG. 15) in order to obtain surface data and other information.

f. The imaging systems of the present invention use extremely simple image processing, where the color of the pixel corresponds to the slope of the object.

g. Features e. and f. combined allow, among others, high resolution, real-time area inspection and line scanning for 3D measurement of specular surfaces and transparent objects.

A gradient element of the present invention may be constructed and configured by anyone of the following non-limiting production methodologies:

a) Create a gradient element (color filter) 202 by printing the desired color pattern on a transparent substrate. This step can be performed using a simple color home printer on a transparency, or with more advanced technologies such as printed colored dots on glass.

b) Coat an optical element with a plurality of filters such as dichroic filters, each having a predetermined spectrum in transmission and/or in reflection.

c) Form a non-uniform thickness element such as a prism made of color material or of a neutral density (ND) material.

d) Attach a polarizer or a color filter to an element having spatially variable transmission properties such as variable ND filters from Reynard Corporation or such as a non-uniform thickness ND material.

e) Attach several elements such as mentioned in steps a) to d) in combination.

In examples a) to e), the gradient element is a passive filter, and is placed either in the illumination or the imaging paths (as will be explained in FIG. 6A). The passive gradient element should be used in conjunction with an active light source having all the characteristics present in the gradient filter. For example, if the gradient element is green and blue, the green and blue must also appear in the light source.

Some examples of active gradient elements are described below:

f) An active patterning device such as a Spatial Light Modulator (SLM), a Digital Micro-Mirror Device (DMD) or an LCD. This device may be placed either in the illumination or in the imaging path, in a transmission or in a reflection mode. This dynamic patterning method enables changing the gradient pattern, as may be required.

g) Active color light sources such as array of LEDs, lasers or supercontinuum lasers, and displays such as OLED displays, image projectors, or pocket projectors h) Light guides such that light sources are emitting light inside one end of the light guides, wherein light is guided up to the other end and exits at the desired position in the inspection system (cf. FIG. 16).

i) Fresnel-like element divided into a large number of micro-prisms and/or micro-lenses, where each micro-structure directs light from one light source towards the optical system. The density of these micro-structures creates the desired spatial distribution for each of the different light sources.

j) A small source, such as a laser beam projected on a diffusive plate or micro-lenses array placed at the Köhler focal plane, will become a collimated beam with controlled incidence angle on the object under test. Scanning the position of the spot is equivalent to scanning the orientation of collimated beams reaching the object under test. A compilation of all the received images reconstructs the object slopes map.

In g), h), i) and j) the patterning element is also the active light source, and will be placed in the illumination path.

The sensor may be any device capable of differentiating between the areas of the gradient element, as for example area sensors, line sensors, single-cell photodiodes and the human eye. The sensor may be composed of a plurality of individual sensors and may include color filters. Examples of such devices are: 3 chips camera, single area sensor with Bayer filter, Foveon three layers technology, 4 chips or more cameras (each chip sensitive to another spectrum) and polarizer attached to a B/W camera. A simple B/W camera may differentiate between areas of a simple gradient element made of spatially variable transmission rate.

FIG. 4 is a simplified pictorial illustration of a ray diagram from a gradient inspection system 400 in transmission mode with a gradient element disposed in the illumination path, in a plane conjugate with the aperture stop of the imaging apparatus, in accordance with an embodiment of the present invention. FIG. 4 shows a schematic example of a possible lens arrangement allowing one to build a gradient inspection system.

System 400 comprises a gradient element 402, either passive or active. Gradient element 402 has a 2D pattern, although only 1D is represented in the figure.

A schematic representation of a possible Köhler illumination 404 is provided, made of two lenses or groups of lenses 406, 408. Other designs are also known in the art. In an embodiment, each point 424, 426 of the gradient source 402 is transformed into a collimated beam reaching the object 410. First, lens 406 transforms each point of the source 424, 426 into a collimated beam 425, 427, and lens 408 images the collimated beams 425, 427 onto object 410. The collimated beams reaching the object are represented by the rays 428, 430, 432, 434. Object 410 is illuminated with plurality of collimated beams, each of them having its own spectrum, relative power, polarization state, switching time and/or incidence angle, but all of them reach the same large area 412 on the object.

It is noted that the simplest gradient Köhler illumination is made of a gradient element placed at the focal plane of a lens, said lens being preferably placed close to the object under test in order not to waste illumination area.

Imaging system 414 is a double-telecentric imaging system (double means telecentric at both sides of the lens). In a preferred embodiment, it is enough that the object side is telecentric; in this drawing the double telecentric configuration is for easier understanding.

Double-telecentric imaging system 414 may be made of at least 2 lenses or group of lenses 416, 418 as is known in the art. The system comprises an aperture stop 420. In this preferred embodiment, 420 is relatively of narrow aperture (in comparison with aperture stop 120 of prior art system 100 of FIG. 1), although completely open aperture may also give desired results in some configurations.

Object 410 is imaged onto a sensor 422. The sensor is connected to a computing system (not shown). An illumination point source 424 belongs to gradient element 402, at its center and an illumination point source 426 is at a side (not at the center) of the gradient element. Points source 424 and 426 create collimated beams and both illuminate the same region 412 of object 410 with a collimated beam, each having a different orientation. Each collimated beam has the characteristics of the respective originating point source 424, 426.

Ray 428 originating from point source 424 reaches point 436 on object 410. The same applies to rays 430, 432, 434 reaching points 436, 438 on object 410. Point 436 has no optical effect, while point 438 has optical effect and may deform an incoming wavefront.

Point 436 does not deflect rays 428 and 432, so that ray 440 equals ray 428 and ray 442 equals ray 432. The ray exiting point 436 parallel to the optical axis 415 of the imaging system 414 came from point 424 on the gradient element 402, and has therefore its characteristics.

In contrast, point 438 does deflect the rays, so that ray 434 becomes ray 446, and ray 430 becomes ray 444. The ray exiting point 438 parallel to the optical axis 415 of the imaging system 414 came from point 426 on the gradient element, and has therefore its characteristics.

The aperture stop 420 is relatively closed, and therefore blocks the rays entering the imaging system 414 not parallel to its optical axis 415. Only rays 440 and 446 can go through the aperture stop 420, while rays 442 and 444 are blocked by it at points 450 and 452.

Points 436 and 438 are imaged onto sensor 422 at points 446 and 448 respectively. Their characteristics are detected by the sensor 442.

Point 448 has the characteristics of the originating point 426, so that its incidence angle on point 438 is known. On the other hand, telecentric lens apparatus 414 lets only parallel rays enter, so that the exit angle at point 438 is known too. From this, the deflection of the ray at point 438 can be calculated. Additionally, the lateral position X, Y of point 438 is known from the obtained image. Thus, to each position X, Y, the direction and quantity of the deviation are definable by using this system. The illuminated region 412 is entirely imaged onto the sensor, and the color of each pixel is the color of the ray that exited the object parallel to the optical axis 415. Since the angle of incidence is known for each ray (due to its characteristics), the deviation produced by the object at this region can be easily calculated. By integrating the results of all pixels, one can almost reconstruct the 3D wavefront, though one cannot know whether there are steps (along a z axis) in the wavefront. From the wavefront, one can determine some optical and/or geometrical properties of the object.

It is noted that, as exemplified by point 436, if the object does not deviate any rays, it will be imaged in a uniform characteristic, which is the characteristic of the center 424 of the gradient element.

The color coding of the gradient elements of the present invention advances in the following way:
- A1: gradient element—the gradient feature is in the spatial domain;
- A2: gradient beams—the gradient feature is in the angular domain;
- A3: gradient illumination reaching the object—the gradient feature is in the angular domain;
- A4: distorted wavefront exiting the object—the gradient feature is in the angular domain;
- A5: aperture stop: the gradient feature and the angular filtering are in the spatial domain; and
- A6: image reaching the sensor—the gradient feature is in the angular domain.

Progressing between field stops and aperture stops is equivalent to progress between the spatial and the angular domains of a given optical system. For this reason, when the gradient element is in the illumination path, the gradient element and the filtering may be disposed in at several planes of an inspection system, but always at planes that are conjugate with an aperture stop of the imaging system. FIG. 6 is an example where the angular filtering is placed in the illumination path, before the object, and the gradient element is placed in the imaging path, after the object. In this latter case, the requirement is that the gradient element has to be placed in one of the aperture stops of the imaging system.

An advantage of illuminating the object with a collimated beam is that any point of the object under test sees exactly the same angular distribution reaching it, independently of its lateral position X, Y and height Z. This feature, added to telecentric imaging, allows measuring the angle of the reflected rays without any unknown geometrical parameters. As opposite, external light sources, such as described in publication US2004184031, reach each point of the object with a slightly different incident angle, the result is that points having same lateral position X, Y and different heights Z reflect the incident ray to different directions.

Attention must be brought to the fact that, contrary to reflection mode, in the case of multiple wavelengths, each wavelength may be deviated differently because the refractive index of the object may be a function of the wavelength. Therefore, when needed, each wavelength may be calculated independently.

The illumination system 404 may have chromatic aberrations that have to be taken into account in the calculation and calibration thereof. If the object under test has a spectral transmission sensitivity (transmission as a function of wavelength), an adequate gradient source has to be chosen to minimize losses and enhance signal to noise ratio. Object transmission/reflectivity may be calibrated and used in the calculation of the wavefront.

Each region from the source may be recognized by the sensor by means of its spectrum, color, RGB value, gray level, polarization state, context of its surrounding and switching time. This is the case, for example, if there is a source where each of its source points has a unique RGB value and if an RGB sensor is used. FIG. 12A shows examples of such continuously varying light source gradients.

For a system based on polarization and not on color, the illumination may be composed of two polarized gradient elements, placed perpendicularly to each other, switched on sequentially, with a single detector. Alternatively, the two polarized gradient elements can illuminate the object simultaneously through a beam splitter, and two cameras with adequate polarized filters attached to them will analyze the beams independently. Such a configuration is illustrated in FIG. 15.

Figure 5A:
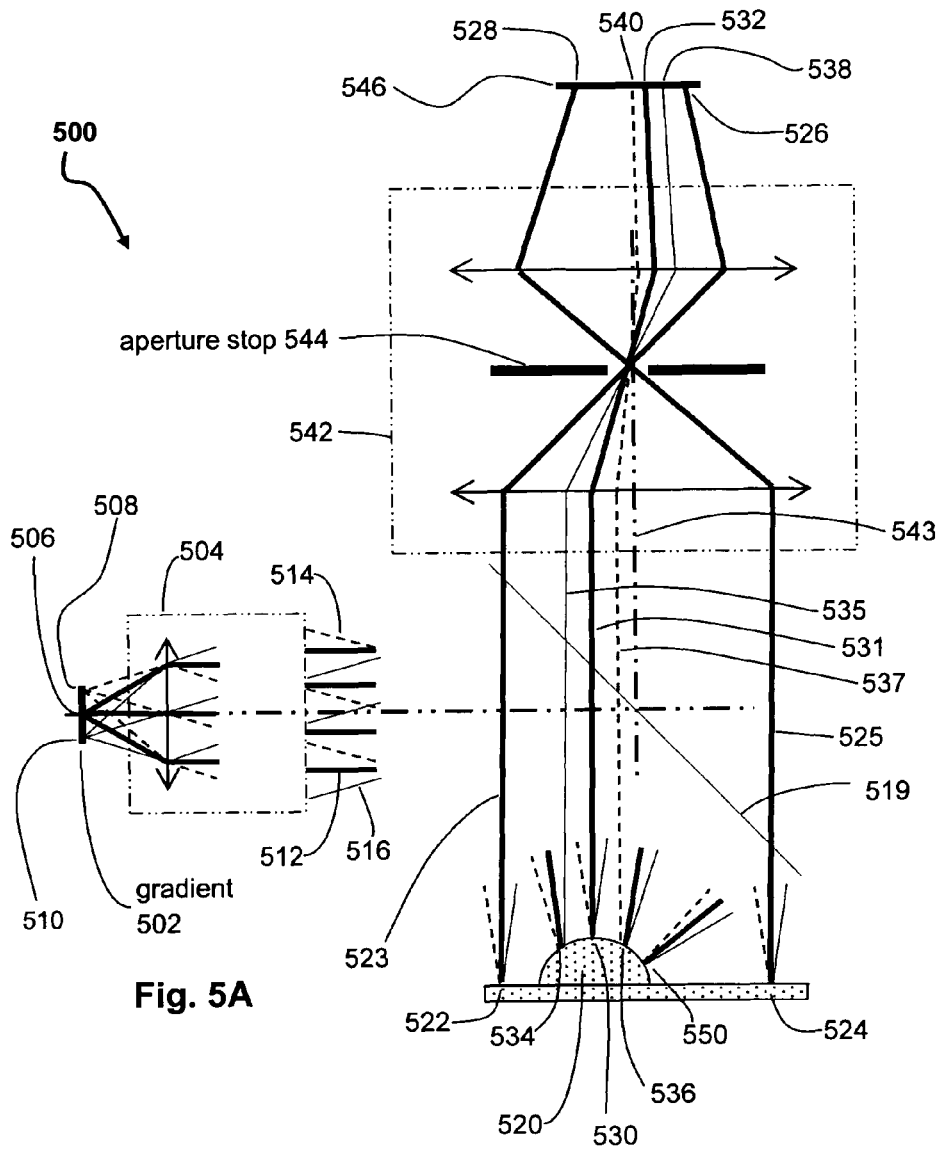

Reference is now made to FIG. 5A, which is a simplified pictorial illustration of a gradient inspection system 500 in reflection, for slope and height reconstruction, using Köhler illumination and telecentric imaging, according to an embodiment of the present invention. Although represented in 2D, it has to be understood in 3D.

System 500 comprises a gradient element 502, which may be active or passive, in combination with a schematic Köhler illumination apparatus 504, such that the exit beams 512, 514, 516 emanating from points 506, 508, 510 are collimated. These beams reach object 520 via beam splitter 519. The incident beams reaching object 520 are not represented in the drawing. Only the reflected beams are represented for clearer understanding. Object 520 is specular, and composed of a bump and a planar surface.

The imaging lens 542 is object-space telecentric, having an aperture stop 544, and imaging object 520 onto sensor 546.

Points 522, 524 are on the planar part of object 520. The incoming beams reaching those points are reflected back in the inverse direction. Only beam 512 is back reflected parallel to the optical axis 543 of telecentric lens 542, into rays 523 and 525. Only rays 523 and 525 will therefore go through the relatively closed aperture stop 544, the other back-reflected rays being filtered out by it. Rays 523, 525 only will reach the points 526, 528 on the sensor 546. Points 526, 528 are the images of points 522, 524, and have the characteristics of the originating point 506 of the gradient element.

In the same way, at point 530 on the top of object 520, only beam 512 is back reflected parallel to the optical axis 543, and only the reflected ray 531 will reach the point 532 on sensor 546. 532 is the image of 530 through the lens 542. Points 526, 528, 532 have all three the same characteristics, meaning the slope of the three points 522, 524, 530 is equal to 0, not depending on their height.

On the other side, the slopes at points 534, 536 are not equal to 0. At those points, only the beams emanating from points 510, 508 of gradient element 502 are reflected parallel to the optical axis 543. Only rays 535, 537 will reach the sensor. The images 538, 540 of points 534, 536 have therefore the characteristics of the originating points 510, 508 of the gradient element.

Point 550 reflects the incident beam at a high angle that misses the aperture stop. In the case wherein the aperture stop is almost closed, the highest measurable object slope is half the highest angle of the illumination beam reaching the object.

As was previously explained in detail with reference to FIG. 4, since the direction of the incidence rays/beams are determined from the characteristics of the imaged point, and the direction of the corresponding reflected/transmitted exit rays/beams is known, the local slope of object 520 at a given point may be calculated. However, it is as yet unknown whether there are steps (along a z axis) in object 520.

Figure 5B:
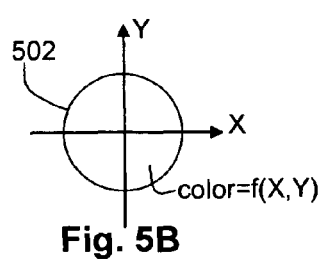

Reference is now made to FIG. 5B, which is a simplified illustration of a spatial distribution of a gradient element 502 of the system of FIG. 5A, according to an embodiment of the invention. Each region of the gradient element defined by an x-y position has predefined characteristics such as color, gray level and polarization state.

Figure 5C:
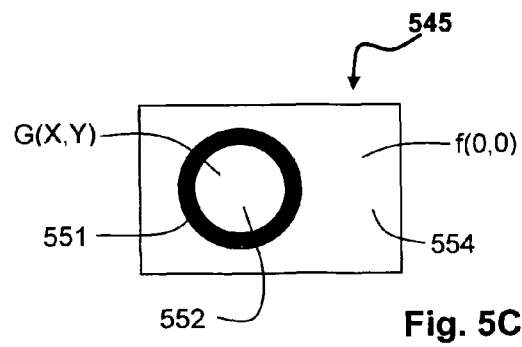

FIG. 5C is an image 545 of object 520 received by sensor 546 in system 500 of FIG. 5A. Image 545 comprises a dark annular region 551 surrounding a central circular light region 552. Area 554 is of a uniform color, which is equal to the color of the center (x=0, y=0) of the gradient element. Dark annular region 551 corresponds to all points such as 550 in FIG. 5A. This region is not imaged because no rays coming from these points reach sensor 546 (FIG. 5A). A color image 552 is made up of points corresponding to points such as 530, 534, 536 on object 520 (FIG. 5A). The colors of each point in region 552 depend on the local slope at those points. In the height reconstruction step, as shown in flow chart 300 (FIG. 3), the flat surface and the central region of object 520 are recognized and reconstructed. However, because of the discontinuity of the image at region 551, the relative difference in height can not be calculated.

FIG. 6A is a simplified pictorial illustration of an inspection system 600 with a gradient element 606 disposed in the imaging system 602, according to an embodiment of the present invention. As was explained for FIG. 4, the gradient element should be placed in one of the aperture stops of the imaging system. FIG. 6 shows examples where the filtering is in the illumination, meaning that the angular extent of the illumination is not large enough to entirely cover the aperture stop of the imaging system during operation.

FIGS. 6B and 6C are intensity diagrams relative to light sources of FIG. 6A.

Inspection system 600 comprises an imaging system 602 with an aperture stop 604 having a gradient element 606 disposed therein.

A first example of light source 626 emits a divergent beam 628. A ray 630 emitted by source 626 reaches object 610 at a point 632. This ray 630 is reflected at point 632 and becomes a reflected ray 634. Reflected ray 634 reaches aperture stop 604 and gradient filter 606 at a point 636, and receives the characteristics of gradient filter 606 at point 636 thereby reaching sensor 612 at point 640. Point 640 is thus the image of point 632, and has the characteristics of point 636 on gradient filter 606. The position of the source 626 is known and the height of point 632 is known with a slight uncertainty, so that the orientation of ray 630 is known with a slight uncertainty. The reflected beam orientation is known thanks to the characteristics of point 640 received on sensor 612. Since the incident and reflected rays are known, one can easily calculate local slope at point 632. FIG. 6B is an intensity diagram of this first example of light source 626. The incident beam 630 is coming from the side, and has a circular angular extent, which comes from the circular shape (not shown) of source 626. The reflected beam 634 may be deformed because of the shape and surface state of the object at point 632. A non-planar surface may deform the beam in the same way spherical and cylindrical mirrors deform a beam. If the surface is not perfectly specular, and has some diffusing component, the angular distribution of the reflected beam may also be enlarged. The reflected beam 634 reaches the region 636 of the gradient filter 606 shown in dotted line. System 600 is therefore able to measure the reflected wavefront coming from source 626, and to reconstruct the slope map of the object using simple geometrical calculations.

In a second example, a small square light source 614 is placed at the focal plane of a lens 615, which creates a collimated beam 616. Beam 616 is reflected at beam splitter 621 and becomes beam 617. The collimated beam 617 has a rectangular angular distribution as shown in the intensity diagram of FIG. 6C. Beam 617 is reflected by object 610 at point 633 and becomes beam 618; beam 618 reaches gradient element 606 at region 619 but is partially occulted (FIG. 6C) because it is near its edge, and then reaches sensor at point 620. Point 620 is the image of point 633, with the characteristics of region 619, said characteristics corresponding to the angle of reflected beam 618. The lateral position X,Y of point 633 is known thanks to the imaging system, incident angle of beam 617 is known (collimated beam), and the angle of the reflected beam 618 is known thanks to the characteristics of point 620 on sensor. System 600 is therefore able to measure the reflected wavefront coming from source 614, and to reconstruct the slope map of the object using simple geometrical calculations.

A third light source creates a grazing beam 624. Its advantage is that it can measure object slopes of up to 45 degrees (with a small aperture stop), or even more with an imaging optics having a high numerical aperture NA. For example, with an NA of the imaging optics of +/−20 degrees, and a grazing incidence of 80 degrees, slopes having 50 degrees relative to the optical axis of the imaging lens can be measured.

FIG. 6A shows ray propagation for easier explanation, although they are extended beams as shown in FIGS. 6B and 6C, and will be further explained in FIGS. 10 and 11.

An advantage of placing the gradient element in the imaging apparatus is that it may require a smaller light source than if it were placed in the illumination apparatus. Another advantage is that this configuration may be of value when complex patterns such as bumps or cavities with multiple facets have to be measured; multiple light sources may be disposed and switched on simultaneously, such that each point of the object preferably reflects only one light source towards the sensor. In this way, high angles of the object can be measured from all their sides altogether, with one single image, allowing even line scanning.

The source illumination has to be preferably but not necessarily disposed and configured such that each point of the object is reached by a thin pencil of light. The source illumination comprises all the characteristics of gradient element 606.

FIG. 6D is a simplified flow chart 650 of a method for surface inspection using the system 600 of FIG. 6A, according to an embodiment of the present invention.

In a set-up step 660, gradient element 606 is placed at one of the aperture stops 604 of imaging lens apparatus 602, in the imaging path. This step may be performed before use of the system or upon manufacture of the system, or during use if the element is active.

In an illumination step 662, one or more light sources 614, 626 illuminate object 610 at a number of different points 632, 633 from a number of angles, simultaneously or sequentially. For example, second light source 626, which may be a white light source emits white light beam 630, which impinges on object 610 at point 632. White light means a light having all the characteristics of the gradient element. The angular extent of these sources 614, 626 should be designed such that the reflected beams do not entirely fill the aperture stop, otherwise the orientation of the reflected beam could not be measured. Sources with narrow angular extent may often be the most appropriate.

In a reflection step 664, the white light beam 630 is reflected as white beam 634, into imaging system 602 through a first lens or group of lenses 603 and onto gradient filter 606.

In a filtering step 666, the white beam 634 is filtered by the gradient filter and receives the local characteristics, such as color, intensity and polarization state of region 636 of the gradient filter thereby generating a colored and/or polarized beam 638.

In a transmission step 667, beam 638 traverses a second lens or group of lenses 605 of imaging system 602 and impinges on sensor 612 at point 640.

In a first processing step 668, sensor 612 receives an image of the entire object under test, each pixel of the image having characteristics corresponding to the slope of the local reflected wavefront. Processor (not shown) creates a wavefront map.

In a second processing step 670, the processor builds slope and height maps from the wavefront data.

Finally, in a displaying step 672, the display (not shown) displays two-dimensional and three-dimensional images of object 610 in real time.

It is noted that in a known gradient system, the characteristics of each pixel may be directly translated into the slope map of the object under test, without formally calculating the wavefront map.

The example shown in FIG. 6 demonstrates the use of a gradient element in the imaging path in reflection mode. It is obvious for those skilled in the art that this configuration is available in transmission mode too.

In standard structured light illumination used for 3D measurement of diffusive surfaces such as publication U.S. Pat. No. 6,556,706, a pattern is projected onto the object under test. Each point of the object is illuminated by another part of the pattern of the structured light. In contrast, in the gradient measurement method, the "structured light" falls within the angular distribution of the beam reaching each point of the object. The method of this invention may therefore be called "Far-Field Structured Light".

Reference is now made to FIG. 7, which is a simplified pictorial illustration of an auto-illuminator imaging system 700 with integrated light sources 710, 712 disposed in one of its physical aperture stop planes 708, according to an embodiment of the present invention.

The aperture stop plane means the entire plane within which the aperture stop is disposed. The aperture stop plane therefore includes, not only the area occupied by the aperture stop of the imaging system itself, but also the area around the aperture stop but within the same plane as the aperture stop and in its close vicinity. A clear aperture 701 is found in the aperture stop plane. By "clear aperture of aperture stop" is meant the region of the aperture stop plane through which the imaging path physically passes. The clear aperture may be smaller than the aperture stop, since numerous optical systems allow closing a diaphragm placed in the aperture stop, thus reducing the diameter of its clear aperture.

By "physical aperture stop" is meant an aperture stop through which at least one imaging beam from an object under inspection passes physically to the sensor, in contrast, for example, with an aperture stop placed in the illumination system.

Auto-illuminator imaging system 700 comprises an imaging lens apparatus 702. The system is used to image any object, such as object 704, which may have any surface state (specular, diffusive, transparent, absorbing), placed at any distance. Lens apparatus 702 images object 704 onto a sensor 706 via clear aperture 701 of one of its physical aperture stops. The sensor may be any device sensitive to light, including, among others, the human eye or cameras connected to computerized systems.

A first light source 710 is placed in the clear aperture of the aperture stop plane. Another light source 712 is disposed in the aperture stop plane, but outside the clear aperture. Both light sources are designed such that light coming back from the object towards the sensor can still be transmitted through the aperture stop.

Both light sources 710, 712 emit light towards the object. Rays 714 are rays emitted by light source 710 and reach object 704. Some rays 716 may be diffused back by the object, but at such angles that they do not reach the aperture stop and sensor 706. Other rays 718, 722, 724 are reflected back off the object and reach the aperture stop. Ray 722 reaches the aperture stop, but without touching light source 710. Ray 722 becomes a transmitted ray 726 and reaches sensor 706 at point 728, which is an image of point 720. In contrast, ray 724 reaches the aperture stop but impinges on light source 710 and is blocked by it. Thus ray 724 does not reach the sensor (the missing transmitted ray is schematically shown as arrow 730). Although arrow 730 does not exist physically, there is still an image at point 728 of object 720, but of a lower intensity than in a case that arrow 730 had existed as a physical ray.

Rays 732 emitted by light source 712 may reach the object, but at higher incident angles than the cone of light defined by the aperture stop. The advantage is that the light source 712 does not block the back-reflected rays. Light source 712 does not fit the strict definition of a bright field because it is outside the clear aperture, but it may still be called bright field because of the similitude of its configuration with light source 710.

It can be seen in FIG. 7 that light source 710 is placed in a physical path of an imaging beam, such as ray 724, thereby obstructing at least one beam 718, 724 coming from object 704 to sensor 706, obstructed beam shown figuratively in as arrow 730.

Auto-illuminator imaging system 700 is unique in that it comprises at least one light source 710, 712 in one of the physical aperture stop planes of the imaging system.

Moreover, it may comprise, according to some embodiments of the present invention, a light source disposed in the physical clear aperture (such as light source 710), so that back-reflected light envelops the light source from all its sides.

Auto-illuminator imaging system 700 is further unique in that light passing from light source 710 and 712, for example, to object 704 travels in a first direction 750, exemplified by optical path of ray 714, through one or more optical surfaces (not shown) of one or more optical elements 740. After having reached object 704, some of the light goes back in a second reverse direction 752 toward the aperture stop plane, passing through a different optical path, exemplified by ray 722, 724 but passing through the same optical surfaces (not shown) in a reverse order.

In auto-illuminator imaging system 700, for each ray/beam which passes in a second reverse direction 752 from object 704 to clear aperture 701 as a transmitted ray/beam through an optical surface, must have previously passed through the same optical surface as a transmitted ray/beam in first direction 750 from light source 710, 712 to the object.

Alternatively, in auto-illuminator imaging system 700, for each ray/beam which passes in a second reverse direction 752 from object 704 to clear aperture 701 as a reflected ray/beam at an optical surface, must have previously passed at the same optical surface as a reflected ray/beam in first direction 750 from light source 710, 712 to the object.

The aperture stop determines the amount of light (energy) traversing the optical system. Each part of the aperture stop that blocks light, reduces the amount of energy reaching the sensor without affecting the nature of the obtained image on the sensor (same effect as closing a diaphragm in a camera). Ideally, when the light source is within the clear aperture, the surface of the aperture stop may both:
  a) emit as much light as possible from as large as possible surface in order to emit as much power as possible; and
  b) transmit as much light as possible from the object towards the sensor, in order to get as much energy onto the sensor as possible.

These two requirements are, in most general cases, incompatible, since the light source itself may block the light reflected back by the object. For this reason, the light source covers only partially the surface of the aperture stop.

As can be seen, auto-illuminator 700 allows eliminating the use of a beam splitter for bright field illuminations. Such configuration is obviously available for any light source placed at one of the physical aperture stop plane of the imaging system. The light goes first through all the optical elements that are placed between the aperture stop where the light source is disposed and the object. Then, some or all the light is coming back from the object to said aperture stop, going through the same elements but in reverse order.

It is noted that the simplest auto-illuminator is a light source attached to a single lens, the aperture stop of an imaging system composed of a single lens being the lens itself.

The advantages of auto-illuminator imaging system 700 are:
  a) Compactness: no need for illumination side-arm that may limit some applications.
  b) No need for beam splitter: a beam splitter may enlarge the length of the imaging lens, and may therefore enlarge the diameter of the optical elements. A beam splitter may also add aberrations to the imaging system. The auto-illuminator may therefore allow an easier and cheaper optical design of the imaging optics.
  c) Efficiency: As explained earlier, the maximum efficiency of a system based on a beam splitter is 25%. For the auto-illuminator, as an example, a light source made of a 1 $mm^2$ LED inside a 3 mm diameter (surface=7 $mm^2$) aperture stop exhibits an efficiency of $6/7$=85% (the light emitted by the source reaches the object without losses, and only 1 $mm^2$ out of 7 $mm^2$ stops the light back from the object). Maximum power is obtained when half of the surface of the aperture stop is filled with light sources, and the other half transmits the back-reflected light. In this case, the maximum efficiency is 25%, but the auto-illuminator is more compact than with the use of a beam splitter.
  d) Shadowing: a light source integrated inside the aperture stop plane illuminates the object with less shadowing than an off-axis illumination.
  e) A light source integrated inside the aperture stop of a zoom lens may move with said aperture stop, such that the size of the illuminated area follows the size of the imaged area.
  f) Lower cost because fewer mechanical and optical elements may be needed than for a system with a beam splitter and with an off-axis illumination.

System 700 may be applied to narrow orifices such as for the purposes of endoscopy, having limited space on the sides for the illumination. Several color light sources, such as RGB LEDs, may be switched on sequentially in order to obtain a color image from a B/W sensor, leading to a higher resolution image than with a color sensor with Bayer filters. Other applications include instruments requiring bright field illumination but having limited space along their optical axis and on their sides. Other applications are for reduced shadowing and/or zoom following illuminations; for example, in the case of flash for consumer cameras. Other applications include requirements for compactness, such as microscopes, pocket microscopes, inspection systems and viewfinders. Numerous applications require miniaturization and cost reduction.

An active light source to be placed at an aperture stop of an auto-illuminator of the present invention, whether inside or outside the clear aperture, may be constructed and configured by one or more of the following non-limiting production methodologies:

a) One or more Solid State Light Sources (SSL such as LEDs, OLEDs and laser diodes) attached to a plate made of a transparent material. Technologies such as, for example, Chip on Board (COB) and SMT may be well adapted because they allow small and thin packaging. The transparent material may be standard optical materials such as BK7, or a transparent diamond for optimized thermal transfer. A second plate may be placed behind the first one, such that water or air can flow between those two plates and cool the SSLs. Current may be brought to the LEDs through connections on the substrate and/or wire bonds. The connections may be as thin as possible to allow maximum transmissive area. Alternatively, the connections may be made of a transparent conducting material such as ITO.

b) One or more SSLs may be attached to standard substrates used in the electronic industry such as PCB, Flex, ceramic, metal-core PCB and other thermal and/or electric conductive materials. Said substrate may be configured such that as much as possible area of the clear aperture is open to let light reach the sensor. The SSL may also be arranged, for example, in a ring shape, outside the clear aperture, for reduced shadowing and efficient thermal transfer.

c) Local optics (lens, prism) may be attached to the SSLs described in a) and b) in order to direct the light to the desired direction and location on the object.

d) The light source may be made of Organic LEDs (OLEDs) and transparent OLEDs (TOLEDs) displays. The pattern and color is easily configurable, and can therefore be changed as often as needed, even within the same application, in order to obtain different information from various illumination types.

The light source may also be a secondary light source such that the primary light source is placed away from the lens. The secondary light source may be placed directly in the clear aperture, enveloped by beams travelling from the object to the sensor. An example of secondary light sources may be the end of one or more light guides, such that the primary light source is coupled to the other end of said light guides. Another example of secondary light source may be one or more flat or curved mirrors placed in the clear aperture such that the mirrors reflect light from the primary light source.

The configuration of the light sources throughout the aperture stop plane may be important, and depends on the application. Here are a few examples of what can be done:

a) one single small light source placed in the aperture stop plane, not necessarily at the center of the aperture stop, to create a collimated beam on the object under test;

b) uniform repartition of small light sources throughout the aperture stop plane, with transparent areas between them, to create a relatively uniform illumination on the object. These light sources may be switched on sequentially and/or simultaneously;

c) one or more independent annular rings in the aperture stop plane, in or outside the clear aperture, to control the angle of the incident beams;

The light source may also be attached to a filter that blocks the spectrum of said light source. The light is emitted towards a fluorescent object that re-emits another spectrum. This re-emitted light alone crosses the filter and reaches the sensor.

No reference was made to colors in FIG. 7, since, obviously, any color arrangement can be used.

FIG. 8 is a simplified pictorial illustration of an auto-illuminator gradient inspection system 800, having an object-space telecentric imaging system 802 with a light source 806 and gradient element 808 disposed in one of its aperture stop planes 804, according to an embodiment of the present invention.

In this system, both the light source and the gradient element are disposed at the aperture stop of the telecentric lens. The light source may be directly attached to the gradient element. The light source 806 is disposed at the center of aperture stop 804 and emits rays 810 towards specular object 812. Since light source 806 is at center of aperture stop 804, the illumination beam 814 reaching object 812 is collimated and parallel to the optical axis (not shown) of telecentric lens 802. The illumination light goes through all the optical elements placed between the aperture stop and the object. At a point 816 having a non-zero slope, illumination beam 814 is reflected into a ray 818, not parallel to the optical axis of lens 802. Ray 818 goes back, in reverse order, through all the optical elements between the object and the aperture stop, until it reaches gradient element 808 at point 820, without touching light source 806. Ray 818 receives the characteristics of point 820, and thereafter reaches a sensor 830 at a point 822, which is the image of point 816 through telecentric lens 802.

On the other hand, point 824 has a slope equal to 0, and the reflected ray 826 is still parallel to the optical axis. It therefore encounters aperture stop 804 at light source 806 and is blocked by it. There is therefore no image 828 of point 824 on the sensor. Dark zones in the obtained image on sensor 830 mean that the object slope is either 0 either too high to let the rays go back to aperture stop 804.

One alternative illumination to the single light source 806 is achieved by placing several light sources, that may be white and single colors, throughout the aperture stop plane. Multiple independent measurements allow, among other, color and system calibration, analysis of complex surfaces (such as non only specular objects and complex 3D objects requiring shadowing reduction), step measurement and analysis of objects with high slopes requiring incident beams at high angles. Another alternative configuration is placing the light source and the gradient elements in two different aperture stops, conjugate of each other.

Active filtering devices such as SLMs and other means described hereinabove may be useful for color and system calibration. For example, one white LED and 2 or more gray levels patterns allow reconstructing the surface without the need for color calibration.

Auto-illuminator gradient inspection system 800 has the advantage of being an extremely compact wavefront analysis system compared to existing technologies, and is useful as well for area sensing as for line scanning applications.

FIG. 9A is a schematic pictorial illustration of absolute height measuring method 900 using the gradient elements of the present invention. This method 900 allows measurement not only of wavefronts, but also of steps. By step is meant a discontinuity in the wavefront, coming from a height difference and/or discontinuity of the object under test.

As was mentioned hereinabove, the gradient apparatus was used to determine slopes but not steps. By adding another independent gradient measurement, it is further possible to use the systems of the present invention to measure steps. Examples of independent measurements are measurements with different convergence and/or with different directions. FIG. 9A demonstrates this method with a non-limiting example with two beams having different convergences in a reflection mode. This method applies also for step measurement of wavefronts in transmission As is seen in FIG. 9A, there are 2 beams with different convergences: a) an incident collimated beam 902 parallel to the optical axis Z 904, and b) a non-collimated beam 906, in this example, a point source. Beams 902 and 906 can be either switched on at different times, or together with 2 independent gradient features. For example beam 902 can be based on 2 colors (red and blue) and beam 906 on 1 color (green), the sensor being an RGB camera. Thereafter, the two gradients can be measured simultaneously. The gradient elements may be in the illumination and/or in the imaging path. Methods for beam combining are shown in FIG. 15.

Both beams reach object 908 at a region 910. Region 910 is at position X, Y, Z, and orientation $\theta$, $\phi$ ($\phi$ is in Y, Z plane, and is not shown). In this example, the object is imaged with a telecentric lens, so that X, Y are known from the obtained image, independently of Z. The collimated beam 902 is reflected with an angle $\alpha$ in the X, Z plane and $\beta$ (not shown) in the Y,Z plane. $\alpha$ and $\beta$ are measurable due to their characteristics on the image of region 910 on the sensor when illuminated by source 902. Both the incident and reflected beams angles are known with an absolute value. $\alpha$, $\beta$ give the information regarding the local tilt $\theta$, $\phi$ ($\phi$ not shown). The height Z is still an unknown using this single measurement. It can be reconstructed by data integration for continuous surfaces. However, this reconstruction does not give information on the absolute height z of the surface nor on the height of local plateaus.

Beam 906 is not collimated, so that it impinges on points of same lateral position X, Y and different heights Z at different incident angles. The reflected beam angle $\gamma$ (the component $\delta$ of the reflected beam in Y, Z plane is not represented) is measured and quantified in absolute value due to its characteristics on the image of region 910 on the sensor (not shown) when illuminated by source 906. Now both $\gamma$, $\delta$ and $\theta$, $\phi$ are quantified in absolute terms, so that angle $\mu$,$\nu$ can be calculated (same for angle $\nu$ in Y, Z plane, not shown). Knowing angle $\mu$, $\nu$ and the position of the source 906 provides absolute information on the height Z of region 910.

FIG. 9B is a simplified flow chart 940 of a step measuring methodology, with reference to FIG. 9A using the gradient elements of the present invention.

In a first projection step 950, a first gradient measurement is performed by projecting beam 902 on object 908. In a first and a second processing steps 952, 954, the reflected wavefront $\alpha$, $\beta$ and then slope $\theta$, $\phi$ and position X, Y of each region or point 910 are calculated, independently of height Z.

In a second projection step 956, a second gradient measurement is performed by projecting beam 906, independent from beam 902, on object 908. In a third processing step 958, the second reflected wavefront $\gamma$, $\delta$ is calculated.

In a forth processing step 960, knowing slopes $\theta$, $\phi$ and second reflected wavefront $\gamma$, $\delta$ at each region 910, the map of the incident angles $\mu$,$\nu$ reaching object from source 906 is calculated. In a fifth processing step 962, incident map angles $\mu$,$\nu$ and second source 906 position allow the calculation of the absolute height map of object.

Thus, the inspection systems of the present invention can provide in real-time the absolute 3D structure of a specular object, including its slope and step data.

FIG. 10 is a simplified pictorial illustration of the angular extent of rays impinging a specular object and reflected back. In several drawings presented in this publication, only single rays are drawn for easier explanation, although they should be represented as full beams. This is the case of FIGS. 4, 5A where the gradient element is in an illumination path. A point 1040 of an object 1030 sees the entire surface of a gradient element (not shown) spread within the angular distribution of a pencil of ray 1010 reaching it. This angular distribution of the gradient element is entirely reflected into pencil of rays 1020. At the aperture stop, there may be a spatial filtering in the angular domain. Since the aperture stop has a finite extent, a finite angular extent of the beam is filtered, rather than a single ray.

This is also true for a gradient element placed in an imaging path. Light sources usually have an extended surface, so that more than a single ray impinges each point of the surface under test. FIG. 10 shows incident beam 1010 coming from the source and reflected back into a beam 1020. Beam 1020 will go through a part of the gradient element. This implies that the light reaching the sensor traverses an extended area of the gradient element, and not only through a single point of it.

FIGS. 10 and 11 would be better seen in 3D. They are available for both cases (gradient element disposed in the illumination path and in the imaging path). In the case wherein the gradient element is disposed in the illumination path, the aperture stop of the imaging system creates the filtering effect. For gradient elements disposed in the imaging path, the extent of the source creates the filtering effect.

Reference is now made to FIG. 11, which is a synthesis of the intensity diagrams of FIGS. 2C, 6B and 6C. Area 1120 represents the angular distribution of a beam coming from a point of the object and focused on the sensor, after having been filtered by either the extent of the source or the aperture stop. Area 1110 represents the angular distribution of the gradient element. The position or center of mass of area 1120 has to be measured relative to area 1110.

That which is received on each pixel of the sensor is the average of the characteristics (for example, an RGB value or a grey level) found in area 1120. Finding the position of area 1120 is straightforward if each point of the gradient element has its own and unique RGB value. Examples of such gradient elements may be for example continuously linearly varying RGB colors or gray levels and arrays of uniform color regions.

The precision of the slope measurement of a point of a specular object is the precision of the measurement of the position of area 1120 relative to the gradient element 1110. It may not be necessary to have a high resolution pattern in gradient element 1110 in order to get a high precision positioning, in the same way as the center of mass of a large spot is calculated although the spot is larger than the pixels constituting it. In some cases, a two-zone or four-zone gradient (FIGS. 12B) may be enough to calculate the center of mass, in the same way as Position Sensing Detectors (PSDs) operate.

In other embodiments of the invention, a gradient source with a known pattern is used such that each point source is recognizable by its surrounding context although it may not be unique.

In cases where slopes need to be detected rather than accurately measured, area 1110 can be made of an array of uniform zones corresponding to the slopes to be detected, such as in FIG. 12C. A two-zoned gradient as simple as 1220 may be, for example, used to visually differentiate between bumps and holes. A gradient such as 1226 may detect the presence and dimension of defects and measure the tilt of micro-mirrors in a MEMS device. It is noted that such discrete gradients may be easier to manufacture and may have well defined and more repeatable regions than continuously varying gradients. Other advantages of discrete gradients may include the reduced cost of illumination, easier and faster data processing (when less colors/power detection is needed), controlled borders (when searching wavefront deviations threshold), uniform regions (when a given range of slopes is searched). Further advantages may become apparent to the practitioner familiar with the art. In other embodiments, discrete gradient elements may be used for automatic detection of given wavefronts. Discrete shapes (such as in FIG. 12C) of the discrete gradient element may be selected to match a known pattern on the objects to be detected. This may be used when each pattern has its own signature, for example.

For an object having a diffusive component in addition to a specular one, the angular extent of the reflected/transmitted beam 1120 is enlarged, but its center of mass may still be measured if area 1120 does not entirely cover area 1110.

Differences in the height of the object under test may cause a slight defocus of the image. Such defocus of the object mixes the characteristics of the defocused region, and therefore reduces the spatial resolution of the measurement. However, regions with slow slope variations may still be accurately measured.

FIG. 12A shows simplified pictorial illustrations of gradient elements 1202, 1204, 1206, 1208 with continuously varying gradient patterns, according to some embodiments of the present invention. Gradient elements 1202, 1204, 1206, 1208 are examples of continuously varying patterns: the dotted lines 1210 are "iso-characteristics" lines. The characteristics vary perpendicularly to lines 1210. These variations are not necessary linear. In some cases (for example gradient 906 in FIG. 9A), a cyclic pattern may enhance the precision of the measurement. The characteristics and their variations are detectable by the sensor(s).

Gradient element 1202 may be an example wherein each line 1210 is uniquely identifiable. Two gradient elements 1202 may be placed perpendicularly to each other to uniquely determine the gradient system. Such configuration may be used with white light and two linearly variable ND filters attached to polarizers.

Gradient elements 1204, 1206, 1208 have two or three independent characteristics recognizable by the sensor(s) of the systems described hereinabove. For example, gradient element 1206 may have three colors red, green and blue (RGB) that may be varied continuously across the gradient elements, superimposed at different angles. Each point of the pattern may be uniquely identified by the sensor due to its characteristics; such as, but not limited to, color, power, surrounding, polarization and switching time. Other continuously varying patterns may be used when appropriate, such as the CIE 1931 color space.

FIG. 12B shows simplified pictorial illustrations of discrete gradient elements 1220, 1222, 1224, 1226 with distinctive areas limited by lines 1230, according to some embodiments of the present invention. Each distinctive area has well-defined uniform characteristics such as color, power, surrounding, polarization and switching time. Other discrete patterns may be used when appropriate.

FIG. 12C shows simplified pictorial illustrations of a gradient element 1240 with discrete gradient patterns 1242 for identification of known object signatures, according to some embodiments of the present invention. Area between patterns 1242 is blanked, which means that no light passes between these patterns.

All the gradient elements shown in FIGS. 12A-12-C may be placed at illumination and/or at imaging paths. The pattern may not necessarily have a circular shape, for example in the case of off-axis illumination where the source can be a dome with a recognizable pattern.

FIG. 12D shows a simplified pictorial illustration of a rectangular gradient element 1250 to be placed in the illumination path of line scanning systems (not shown), according to some embodiments of the present invention. The gradient element 1250 may be rectangular. The Köhler illumination may be asymmetrical, for example cylindrical.

It is noted that, when appropriate, the gradient patterns may have blanked regions for better calibration/detection. Optionally, some blanked patterns may be added in order to easily detect given illumination angles, to calibrate the system, or eliminate some undesired illumination angles. For example, removing 0 degrees incidence angles can be used to detect only defects having a slope higher than a given value (slope threshold) on a planar surface, or to eliminate unwanted reflection from a flat or curved surface of a transparent material that needs not to be measured. The choice of the pattern and type of gradient (color, polarization, time, blanked) matches the type of the test object and the requirements of the application.

It is particularly noted that, in contradistinction to prior art Rheinberg filters such as described above in relation to FIG. 1B and which are used to emphasize visual image contrast, the gradient elements described above in relation to FIGS. 12A-C are used to provide in real-time wavefront analysis, 3D structure, slope data and step data. Accordingly, the gradient elements of the present invention have graduated varying optical properties configured to provide illumination beams having a number of different optical characteristics. Prior art Rheinberg filters, on the other hand, typically have distinctly colored areas configured only to enhance contrast. The difference between these is well known to the users of optical systems.

Other types of spatially variable prior art filters placed at the aperture stop of illumination systems exist and are called "apodizing filters". Typically, these prior art filters modify the intensity variations of the light source in order to get a flat top uniform angular illumination, which is quite the opposite of the requirements of the systems and methods of the present invention.

Reference is now made to FIG. 13, which is a simplified pictorial illustration of a ray diagram of a gradient inspection system 1300 in reflection mode, according to an embodiment of the present invention.

A light beam 1302 is cast in the direction of a beam splitter 1304. Beam splitter 1304 receives a ray 1320 from light beam 1302 and redirects it as ray 1322 towards an object 1308 via a point 1324 on a gradient element 1306 and via a first lens 1312, from where it exits as a ray 1326. The gradient element is placed at one of the aperture stops of the imaging system. Ray 1326 impinges perpendicularly onto the object at a point 1328. Due to the perpendicularity of incidence of ray 1326, a reflected ray 1330 is reflected back along the path of ray 1326 and also therefore via point 1324. Ray 1330 exits the gradient element as ray 1332 and passes through the beam splitter and through a second lens 1314. The ray exits the second lens 1314 as a ray 1334 and reaches a sensor 1310. Any other ray that does not reach the object at a normal angle of incidence, will go through two different regions of the gradient element.

A suitable gradient element may filter out all the paths that do not go through the same point on the gradient element in both directions, so that the characteristics of the ray 1334 of point 1328 are the ones of point 1324. The color (RGB or gray level GL) of each pixel of the obtained image represents a given slope on the object. A gradient element such as 1226 (FIG. 12B) may also be useful for some applications based on system 1300. System 1300 may also be built with an integrated light source such as shown in FIG. 8. Two aperture stops are needed in this case, one for the light source, the other one for the gradient element.

The advantage of this configuration is that the highest measurable slope is the highest angle of illumination and/or imaging.

Reference is now made to FIG. 14, which is a schematic pictorial illustration of a ray diagram in a general case of a gradient inspection system in a reflection mode 1400, according an embodiment of the present invention.

FIG. 14 shows a very general configuration of a gradient inspection system in order to show that the invention can be applied to almost any existing imaging apparatus in order to transform it into a wavefront analyzing tool. A beam is obtained by placing gradient element 1402 in front of lens 1404. The two points 1420, 1422 belong to gradient element 1402. A specular object 1406 may be tested at a local region 1408. Within the local region under inspection, a beam from each point 1420, 1422 along the extended gradient element 1402, reaches the object at a different angle of incidence. Consequently, the beam from each point source 1420, 1422 is reflected in a different direction. It is noted that the more specular the region under test, the narrower the beam reflected therefrom. The characteristics of the image of region 1408 on the sensor will be closer to the characteristics of the reflected beam 1432 than those of reflected beam 1430. Where the local region is less specular, light from a larger area of the gradient element may reach the sensor 1412. For a perfectly Lambertian object, beams from all the points throughout the gradient element may be transmitted with the same quantity to the sensor, and it may be impossible to differentiate the originating point at the gradient element.

It is noted that most known imaging systems, in reflection and/or in transmission mode, may be converted into 3-D wavefront inspection systems by the use of at least one gradient element of the present invention and a suitably arranged light source.

Collimated illumination and telecentric imaging usually allow optimized mechano-optical configuration for the inspection of specular and transparent objects, as well as easier image processing, but these are not mandatory in order for the gradient methods of the present invention to be operative.

In a non-collimated illumination, each point of the object sees a similar, but not identical, angular distribution, which means that the same pattern, either gradient or uniform, is received, but with an incidence orientation depending on the position of said point.

In a collimated illumination, each point sees the same angular distribution, independently of its lateral and height position.

Reference is now made to FIG. 15, which is a schematic illustration of a general setup of a gradient inspection system 1500 for use in calibration, superimposition of images and analysis of complex surfaces, according to an embodiment of the present invention.

System 1500 is a general setup of wavefront analysis inspection systems of the present invention. It should be understood that system 1500 is extremely versatile and may include a number of different configurations including several gradient elements and several illumination and imaging apparatus in various combinations. System 1500 can be used for calibration/superimposition/concomitant display of video images and/or for three dimensional complex surfaces analysis. It can be seen in the figure that several light sources 1502, 1504 and several imaging apparatus 1512, 1514, 1516 illuminate and image an object 1510. Imaging apparatus include imaging systems and sensors. This may be in a simultaneous or sequential manner. Each imaging apparatus may have different characteristics and may be constructed and configured to work simultaneously, or have common characteristics and work sequentially with same and/or other sensors in the system. The system comprises a number of beam splitters and/or dichroic filters 1506, 1508, 1518.

System 1500 may be applied to many different wavefront analysis inspection methodologies. Some examples of the methodologies are provided hereinbelow:

a) Real-Time Concomitant Display of a 2D and 3D Image

Light sources 1502, 1504 are, according to some embodiments, designed to emit successively two different types of lights. For example, these may be a white light and a color gradient light. The switch between the two may be implemented by suitable electronics (not shown). This electronics is synchronized with the sensors, which in this case are color cameras. For example, every alternating frame is taken with the white light, and the intervening frames between the alternating frames are taken with the gradient light. The white light is displayed as a standard 2D visual image on a computer screen, and the 3D profile is displayed in parallel to the standard image on the screen (such as display 228 (FIG. 2A)).

Such apparatus can be used in microscopy, for example.

b) Wavefront Analysis Inspection System Color Calibration

The invention is based on the ability to detect characteristics of the gradient elements, but object 1510 may also have an effect on those characteristics (such as color and polarization). These effects should be known in advance and/or calibrated. Three non-limiting methods of calibration are provided herewith:

Calibration Method 1:

With reference to FIG. 15, two images may be captured with and without a gradient element (not shown). A reference image, captured without the gradient element, records the characteristics of each point of the object. For example, light sources 1502 and 1504 can be:

a white light and a color gradient (when a gradient is use in the illumination)

a small and a large source (when a gradient is used in the imaging)

An alternative is to mix two complementary spectra. The gradient is for example based on tree narrow bands RGB, while the calibration light is white light from which said RGB bands are removed. The color of the object under test is reconstructed by spectral interpolation of the calibration light. Both analysis and calibration images can also be produced at the same plane with the use of an active light source and/or active gradient element such as a DMD, LCD or pocket projector.

Calibration Method 2:

An array of small balls (not shown) may be placed in place of object 1510 as a reference image. The balls have the same surface characteristics as the object under test. In this way, system 1500 may be calibrated using the predefined characteristics of the small balls. The image of the balls provides calibration data (characteristics in function of angle and position of object) of the system.

Calibration Method 3:

A reference image of an object of known characteristics is captured and reference data are defined. Thereafter, an object under test is imaged and the image thereof is compared with the reference data to define the analyzed object characteristics.

c) Inspection System for Complex Surfaces

For example, light source 1502 is a gradient illumination with a first spectrum and light source 1504 is a standard structured illumination for diffuse surface testing with a different second spectrum, non-overlapping with the first spectrum.

In this example, imaging apparatus 1514 is constructed and configured to detect the spectrum of light source 1502 and imaging apparatus 1516 is constructed and configured to detect the spectrum of light source 1504. This system setup enables the measurement of a surface having both specular and diffusive components in real time concomitantly.

Another example using this system in a different configuration (lacking a second light source 1504) is as follows:

Light source 1502 comprises a gradient element (not shown) having first spectral characteristics in a conjugate plane of an aperture stop (not shown) of imaging apparatus 1514. Light source 1502 comprises a patterned filter having spectral characteristics different from those of the gradient element (not shown) for standard structured light at a conjugate plane of object 1510 under test. Using this configuration, both specular and diffuse kinds of measurements of surfaces states can be performed simultaneously by system 1500, using a single light source.

Another example of an application of system 1500 is a line scan performed with white light in system 1500 comprising only one line light source 1502. Imaging apparatus 1514 comprises a gradient filter (not shown) in the imaging path. This system may be used for 3D measurement based on triangulation for diffuse surfaces and gradient measurement for specular surfaces simultaneously. When the white light from source 1502 impacts on a diffuse surface, the reflected light is angularly diffused and covers the entire gradient element in sensor 1514 such that white light is received by the sensor. When white light from source 1502 impacts on a specular surface, the reflected light has a narrow angular distribution and impacts only on a specific part of the gradient element in imaging apparatus 1514; such that light of certain spectral characteristics is received by the sensor, thereby determining the local slope of the surface of object 1510.

Another example of an application of system 1500 is double line scanning. A first line scan based on gray levels gradient element in one direction (such as for example element 1202 in FIG. 12A) is performed. Then, a second line scan based on another gray level gradient element 1202, but in a perpendicular direction to the first one, is performed. The compilation of these two received images provides 3D data of the scanned object. The advantages of this configuration are the use of a single spectrum for the illumination, and the use of a B/W camera with higher resolution and lower cost than a 3-chip sensor.

Reference is now made to FIG. 16, which is a simplified pictorial illustration of an example of a discrete active gradient light source 1600 built with light guides 1612, 1614, 1616 and 1618. Light guides 1612, 1614, 1616 and 1618 are, for example, independent concentric annuli which enable passage of light from a first end 1602 to a second end 1604 of the active gradient light source 1600. Alternatively, the light guides may be constructed of other shapes and dimensions, as exemplified by the gradient elements shown in FIG. 12B.

Each light guide may comprise one or more solid state light sources 1606, 1608 and 1610 (SSLs) such as LEDs and/or lasers at a first end thereof. Each one or more solid state light sources 1606, 1608 and 1610 (SSLs) may be constructed and configured to emit a certain spectrum, which may be different from the other SSLs. Light entering at one end 1602 of one of the light guides remains in the same light guide until it reaches and exits the other end 1604, without leaking to the other light guides. Each light guide exit surface emits a controlled and variable color, independently from the other light guides.

The light guides may be rigid, made of glass or plastic, or flexible, made of bundles of fiber optics. In the case of fiber optics bundles, the fibers may be arranged so that the exit surface can be considered as continuously varying pattern made, for example, of three colors.

The active gradient light source 1600 may be disposed with the emitting end 1604 at one of the aperture stops of an imaging system, such as the systems described hereinabove. It may also be used as a dynamic Rheinberg illumination as is known in the art, without gradient measurement. It should be understood that the wavefront analysis inspection systems of the present invention provide advantages over the prior art Hartman Shack, inter alia, as defined in Table 1.

TABLE 1

Comparison of advantages of the systems of the present invention over prior art Hartman Shack systems.

| | HARTMAN SHACK-PRIOR ART | PRESENT INVENTION |
|---|---|---|
| spatial wavefront resolution limitation | micro-lenses pitch | sensor spatial resolution |
| dynamic range limitation of the measured slope | focal length and pitch of micro-lenses (limit reached when spots touch each others) | sensor dynamic range |
| sensor | gray level images enough | sensor capable of differentiating between the areas of the gradient element |
| calculation | based on centers of mass of spots | based on RGB or gray level GL value of pixels on image |

Examples of Applications

Various applications of the systems and methods, exemplified hereinabove, of the present invention include:

- replacement of Zygos, Hartman-Shack and other wavefront measurement tools
- transformation of any microscope into a 3D device
- automated inspection of specular and quasi-specular objects such as glass, wafers, FPD industry, PCB industry, solder joints, ball grid arrays
- inspection of MEMS devices
- measurement of thickness of thin film on specular objects
- measurement and quality control of lenses or group of lenses in transmission and reflection (spherical and aspherical, cylindrical . . . )
- in-line quality control of plastic elements during their productions
- measurement of reflective molds
- real time analysis of ongoing 3D process, such as biologic transparent samples
- ophthalmic lenses (progressive, contact, intra-ocular) and their reflective molds
- 3D measurement of teeth
- measurement of metallic shining parts
- creation of 3D patterns that can only be read/decoded with an adequate gradient element placed in a gradient inspection system (tags, counterfeiting . . . )
- new type of optical data storage, where each pit is intentionally tilted. This tilt adds a new dimension to each pit and new storage capacity to the media. Gradient inspection system can measure/detect these tilts with a single-cell photodiode or with an area sensor for parallel data reading
- measurement of facets of a diamond press-proof, by measuring the volume of the cells in gravure cylinder engraving autofocus measurement measurement and quality control of Fresnel lenses, diffractive lenses, micro-lenses, micro-lenses array and other micro-structured on specular devices measure of atmospheric turbulences, where the light source may be a distant object, such as a star and a target on Earth, and the object under test is the air between the distant object and the analyzing apparatus. A reference color image is grabbed in parallel with a gradient measurement.

measurement of 2D and 3D wavefront changes in aerodynamics experiments measure the intensity [W/sr] profile of a light source under test (for example using a polarized gradient element)

The references cited herein teach many principles that are applicable to the present invention. Therefore the full contents of these publications are incorporated by reference herein where appropriate for teachings of additional or alternative details, features and/or technical background. In the claims, the word "comprise", and variations thereof such as "comprises", "comprising" and the like indicate that the components listed are included, but not generally to the exclusion of other components.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

The invention claimed is:

1. A gradient inspection system constructed and configured to inspect a wavefront exiting an object, the system comprising:
    an illumination system constructed and configured to illuminate said object such that an angular coverage of light comprising a same pattern is received by each point of said object;
    an imaging system constructed and configured to image said object onto an image plane;
    at least one aperture stop of said imaging system;
    at least one conjugate plane associated with said at least one aperture stop;
    a gradient element comprising at least two distinct areas, each area enabling a passage of light of at least one of a defined spectrum and power therethrough, said gradient element being disposed in said at least one conjugate plane; and
    a sensor disposed in said image plane of said imaging system, said sensor comprising at least one pixel, said at least one pixel receiving an image of at least one related region of said object, wherein said sensor is capable of differentiating between said at least two distinct areas of said gradient element, and wherein at least one of a color characteristic and a gray level characteristic of said at least one pixel enables reconstruction of said wavefront at said at least one related region of said object, and wherein said gradient inspection system is thereby adapted to inspect properties of said object.

2. A gradient inspection system according to claim 1, wherein said object comprises a specular surface, and wherein a slope map of said object is inspected.

3. A gradient inspection system according to claim 1, wherein said object comprises a transparent area, and wherein optical properties of said object are inspected.

4. A gradient inspection system according to claim 1, wherein said at least one conjugate plane is in said illumination system.

5. A gradient inspection system according to claim 1, wherein
    said gradient element has a spatial distribution f(x,y) made of at least two distinct spectra,
    said at least one conjugate plane is in said illumination system,
    each point of said object receives a same angular distribution of light f(alpha,beta) corresponding to said spatial distribution f(x,y), independently of a lateral and height position of said point, and
    said imaging system comprises an object-side telecentric lens.

6. A gradient inspection system according to claim 1, wherein said gradient element comprises one passive element.

7. A gradient inspection system according to claim 1, wherein said imaging system comprises an optical axis, and wherein said at least one aperture stop adapted to block rays not parallel to said optical axis from entering said imaging system.

8. A gradient inspection system according to claim 1, wherein said imaging system comprises an object-side telecentric lens.

9. A gradient inspection system according to claim 1, wherein each point of said object receives a same angular distribution of light, independently of a lateral and height position of said point.

10. A gradient inspection system according to claim 1, wherein said sensor comprises at least one line sensor.

11. A gradient inspection system according to claim 1, further comprising an independent gradient inspection system for measuring absolute three-dimensional structure of said object.

12. A gradient inspection system according to claim 1, wherein one single image of said object is required for said reconstruction of said wavefront, thus allowing real-time inspection of said object.

13. A gradient inspection system according to claim 1, wherein said gradient element has a spatial distribution f(x,y) made of at least two distinct spectra and is disposed in said illumination system.

14. A gradient inspection system according to claim 1, wherein at least two areas of said at least two distinct areas enable the passage of light of a same spectrum, and wherein said differentiation between said at least two areas of said at least two distinct areas comprises means for recognition by context of surrounding.

15. A gradient inspection system according to claim 1, wherein said gradient element comprises at least one active patterning device.

16. A gradient inspection system according to claim 1, further comprising an auto-illuminator configured such that:
    said imaging system comprises at least one optical surface, and
    a light source of said illumination system is placed in a physical aperture stop plane of said imaging system, wherein light travels in a first direction from said light source to said object via said at least one optical surface, and wherein, after having reached said object, said light goes back in a second reverse direction, in a reverse order, towards said physical aperture stop plane via said at least one optical surface, and reaches said sensor.

17. A gradient inspection system according to claim 15, wherein said at least one active patterning device comprises a display device constructed to be an active light source of said illumination system.

18. A gradient inspection system according to claim 16, wherein said light source is placed in a clear aperture of said physical aperture stop plane of said imaging system.

19. A method for inspecting an object, the method comprising:
  disposing a gradient element in an illumination system, said gradient element comprising at least two distinct areas, each area enabling a passage of light of at least one of a defined spectrum and power therethrough;
  disposing an imaging system comprising an aperture stop, such that said gradient element and said aperture stop are in conjugate planes;
  disposing said object at an object plane of said imaging system;
  disposing a sensor at an image plane of said imaging system, said sensor being capable of differentiating between said at least two distinct areas of said gradient element;
  receiving an image comprising at least one pixel, said pixel being related to a region of said object, wherein at least one of color characteristics and grey level characteristics of said pixel corresponds to a wavefront exiting said region of said object; and
  reconstructing from said wavefront a map of properties of said object.

20. A gradient inspection system constructed and configured to inspect a wavefront exiting an object, the system comprising:
  an illumination system constructed and configured to illuminate said object such that an angular coverage of light comprising a same pattern is received by each point of said object;
  an imaging system constructed and configured to image said object onto an image plane;
  at least one aperture stop of said imaging system;
  at least one conjugate plane associated with said at least one aperture stop;
  an active patterning device comprising at least two distinct areas, each area enabling the passage of light at different times therethrough, said active patterning device being disposed at said at least one conjugate plane; and
  a sensor disposed in said image plane of said imaging system, said sensor comprising at least one pixel, said at least one pixel receiving an image of at least one related region of said object, wherein said sensor is capable of differentiating between said at least two distinct areas of said active patterning device, and wherein time characteristics of said at least one pixel allows reconstruction of said wavefront at said at least one related region of said object, said gradient inspection system thereby being adapted to inspect properties of said object.

* * * * *